United States Patent [19]
Inoue

[11] Patent Number: 5,242,452
[45] Date of Patent: Sep. 7, 1993

[54] DEVICE FOR COLLAPSING AN APPLIANCE COLLAPSIBLE FOR INSERTION INTO HUMAN ORGANS

[76] Inventor: Kanji Inoue, 98-13, Miyazaki-cho Simogamo, Sakyo-ku, Kyoto-shi, Kyoto 606, Japan

[21] Appl. No.: 998,147

[22] Filed: Dec. 29, 1992

Related U.S. Application Data

[60] Division of Ser. No. 920,915, Jul. 28, 1992, which is a continuation-in-part of Ser. No. 768,195, Oct. 11, 1991, abandoned.

[51] Int. Cl.⁵ .............................................. A61B 17/12
[52] U.S. Cl. .................................. 606/108; 606/148; 606/198
[58] Field of Search ................. 623/1, 12; 600/36, 37; 606/108, 144, 148, 191, 194, 198; 604/8, 104; 128/838, 840

[56] References Cited

U.S. PATENT DOCUMENTS

| | | | |
|---|---|---|---|
| 4,512,338 | 4/1985 | Balko et al. | |
| 4,739,762 | 4/1988 | Palmaz | 623/1 X |
| 4,856,516 | 8/1989 | Hillstead | 623/1 X |
| 4,873,978 | 10/1989 | Ginsburg | 606/198 |
| 4,878,906 | 11/1989 | Lindemann et al. | 623/1 |
| 4,913,141 | 4/1990 | Hillstead | 606/108 |
| 4,998,539 | 3/1991 | Delsanti | 606/198 X |
| 5,041,126 | 8/1991 | Gianturco | 623/1 X |
| 5,129,912 | 7/1992 | Noda et al. | 606/148 X |
| 5,147,370 | 9/1992 | McNamara et al. | 606/108 |
| 5,176,661 | 1/1993 | Evard et al. | 606/194 X |

FOREIGN PATENT DOCUMENTS

| | | |
|---|---|---|
| 63-160644 | 7/1988 | Japan. |
| 63-257576 | 10/1988 | Japan. |
| 64-86983 | 3/1989 | Japan. |
| 8303752 | 11/1983 | PCT Int'l Appl. ............ 600/37 |
| 1217402 | 3/1986 | U.S.S.R. ...................... 623/1 |

*Primary Examiner*—Randall L. Green
*Assistant Examiner*—Mary Beth O. Jones
*Attorney, Agent, or Firm*—Wegner, Cantor, Mueller & Player

[57] ABSTRACT

An artificial body vessel to be inserted into a human organ is collapsed and introduced into a catheter, which is brought to a required position in the human organ, where the artificial body vessel is released therefrom. A pair of foldable, elastic wire rings 10 are provided at the opposite ends of the artificial body vessel. A plurality of connecting wire rings bridge the end wire rings 10. A plurality of intermediate wire rings 12 bind and keep the connecting wire rings 11 transformed in a generally elliptical shape. The end wire rings 10, the intermediate wire rings 12 and the connecting wire rings 11 are folded by means of a string passed through loops to collapse the artificial body vessel 7. The collapsed artificial body vessel 7 is inserted into a catheter. At the objective position of the blood vessel the artificial body vessel 7 is released, so that the resiliency of the end wire rings 10, the intermediate wire rings 12 and the connecting wire rings 11 restores the artificial body vessel 7 to its original tubular shape. The artificial body vessel 7 is released by means of a tube, formed with a side window adjacent its front end, containing a wire which extends along the side window.

10 Claims, 22 Drawing Sheets

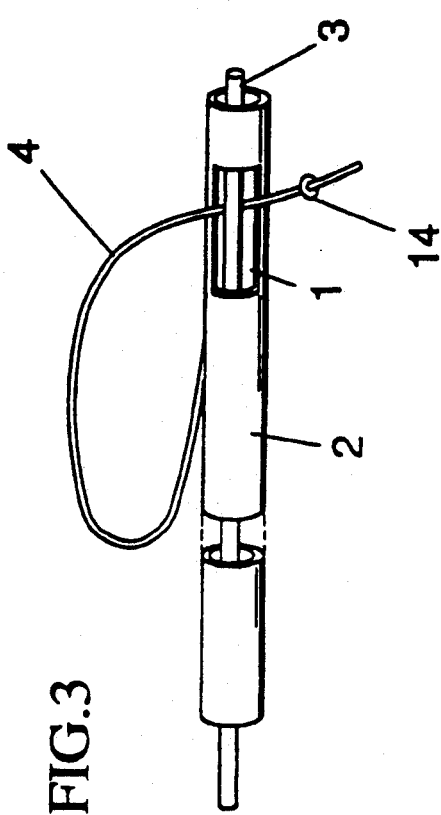
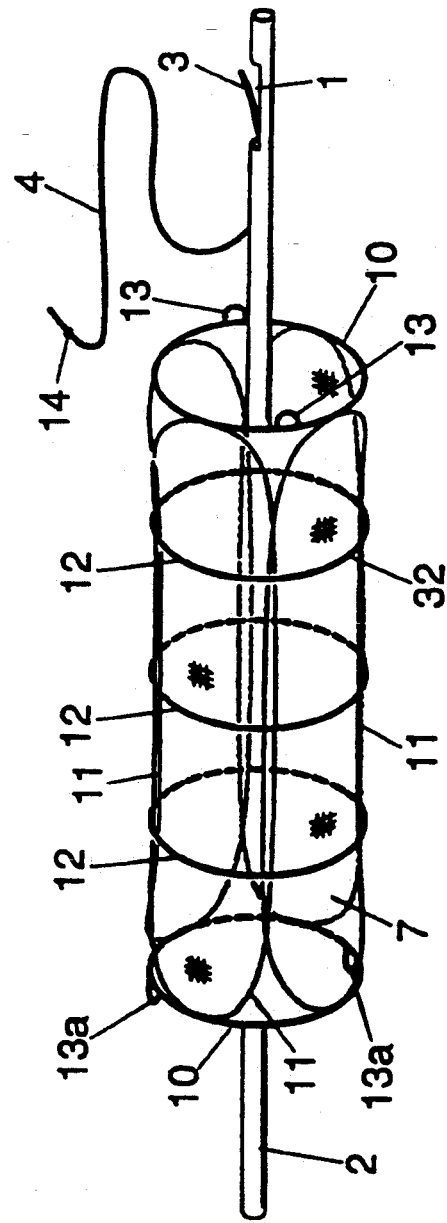
FIG.3
FIG.4

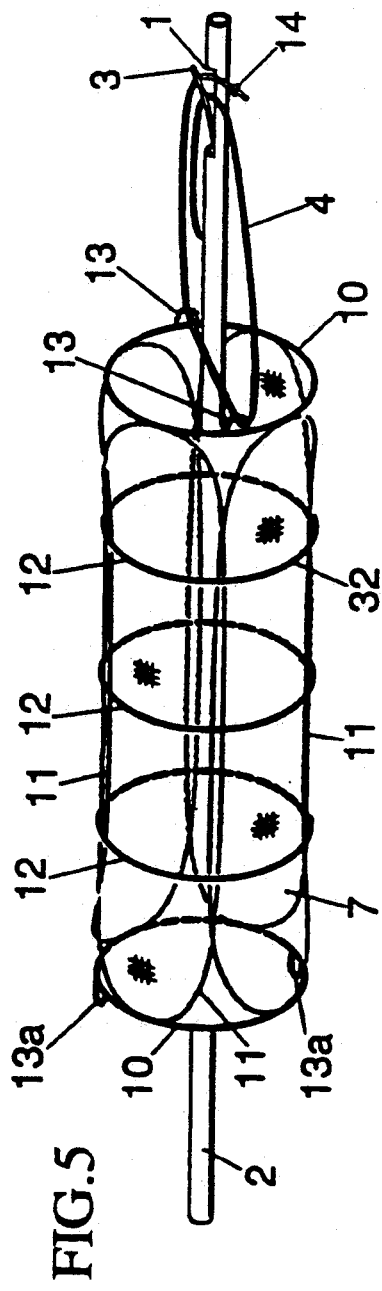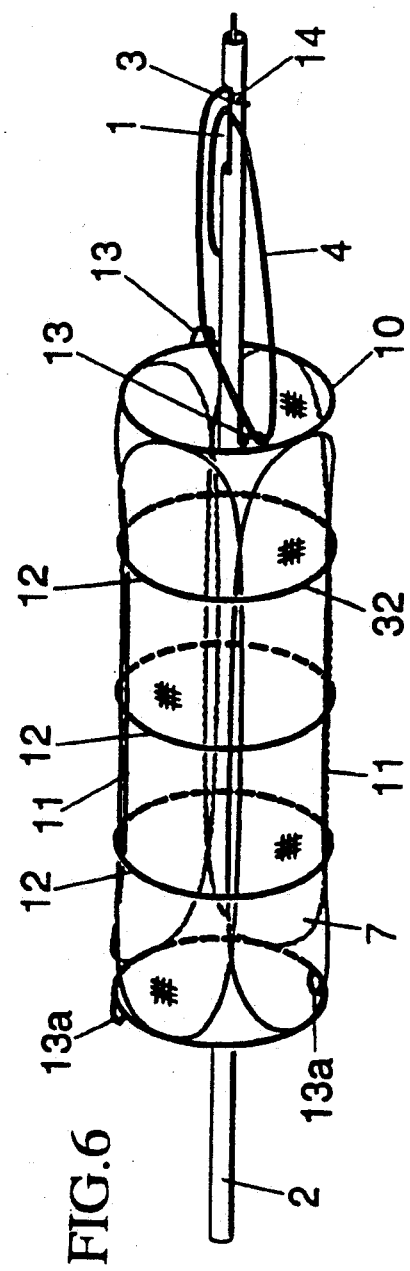

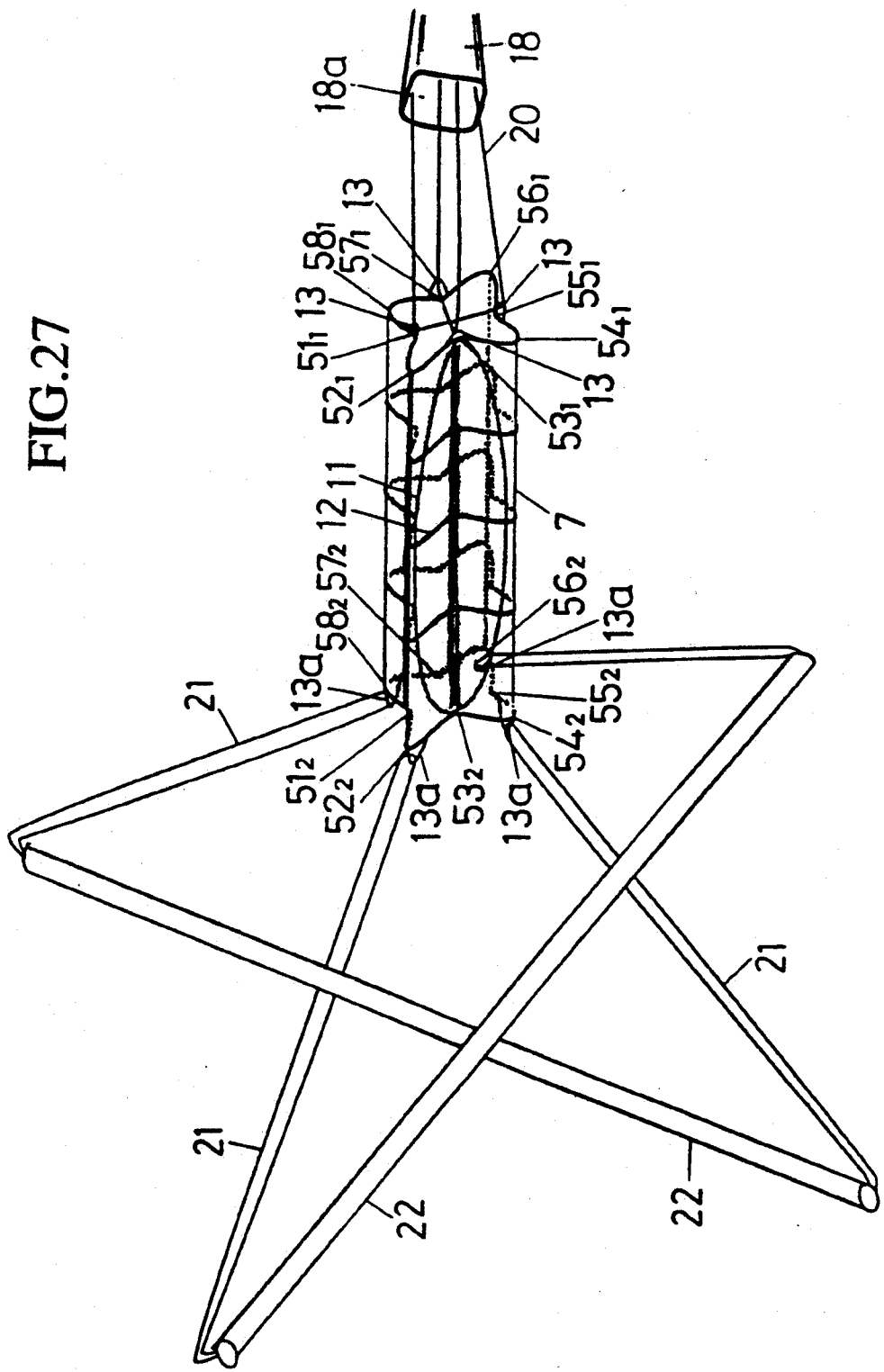

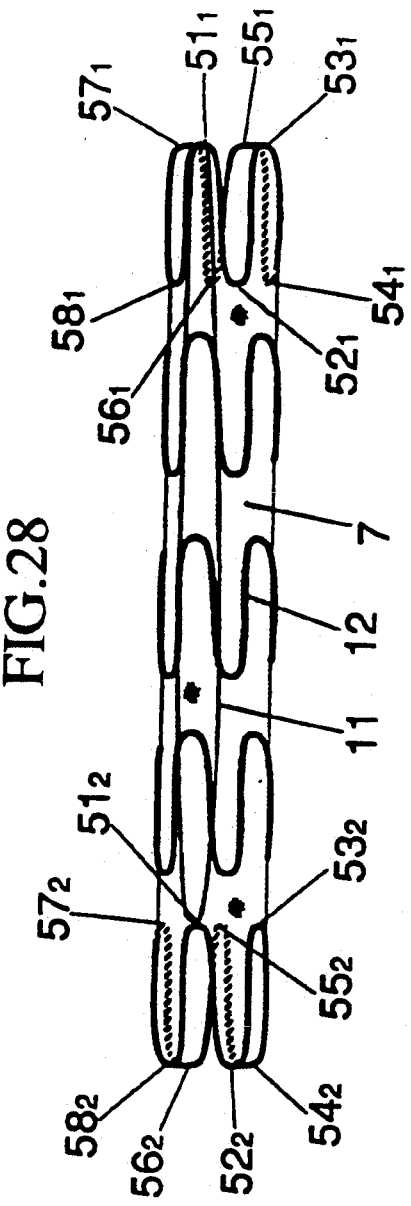
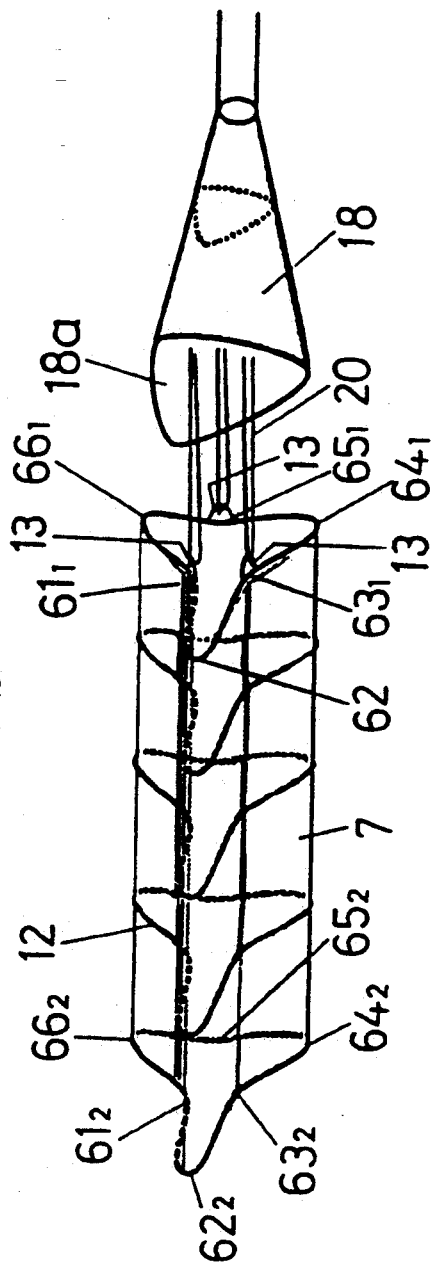

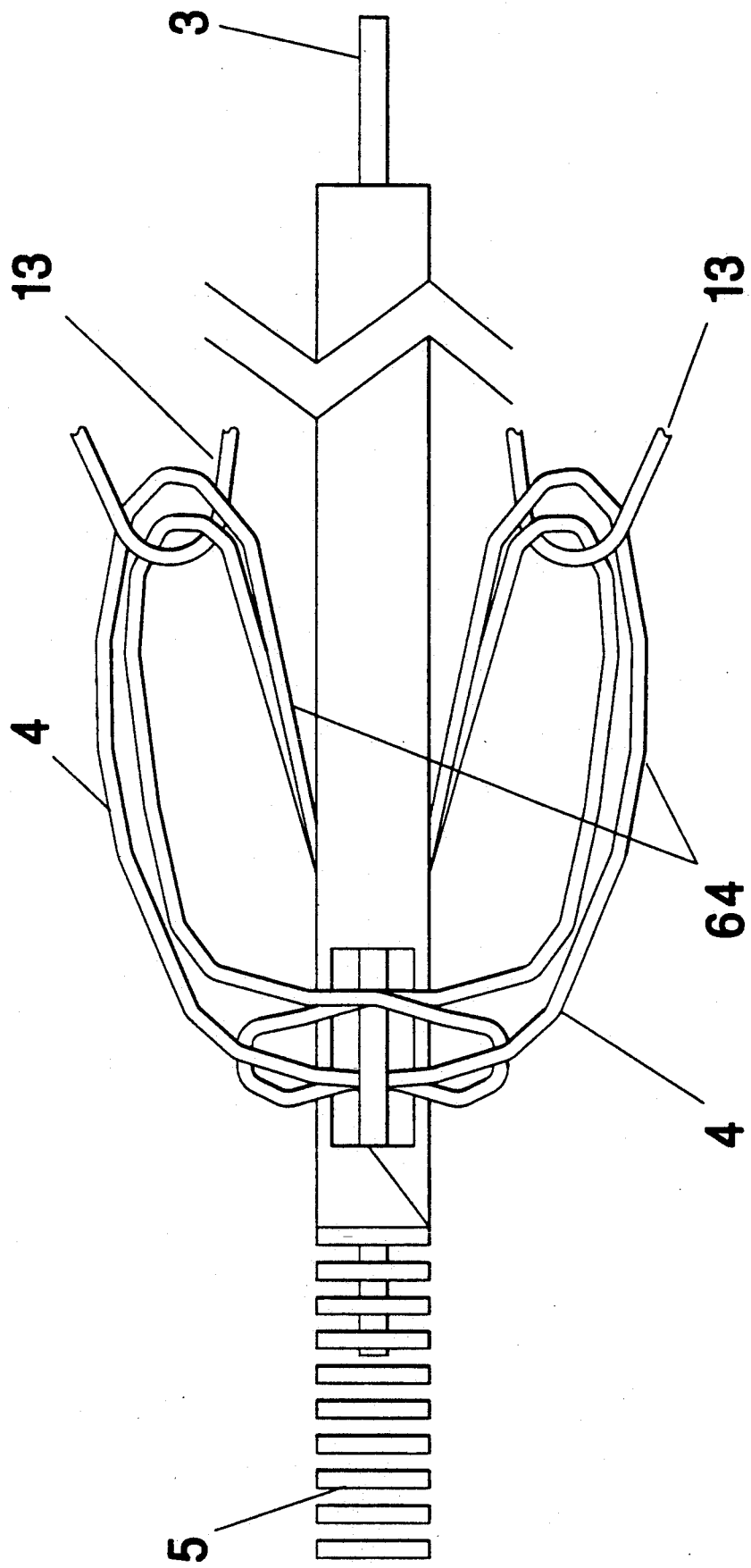

DEVICE FOR COLLAPSING AN APPLIANCE COLLAPSIBLE FOR INSERTION INTO HUMAN ORGANS

This application is a division of Ser. No. 07/920,915 filed Jul. 28, 1992; which is a continuation-in-part of Ser. No. 07/768,195 filed Oct. 11, 1991, now abandoned.

TECHNICAL FIELD

This invention relates to appliances for medical treatment and, more particularly, to an appliance collapsible for insertion into human organs and capable of resilient restoration, and to a device for collapsing the appliance.

BACKGROUND ART

At present, treatment of, say, aortic aneurysms is conducted by implanting artificial blood vessels. In particular, the portion of a blood vessel which has an aneurysm is removed by resection, and an artificial blood vessel is implanted in place of the resected portion and connected to the remaining blood vessel by suturing.

The above-mentioned method of surgically implanting artificial blood vessels for treatment of aortic aneurysms, however, is highly dangerous. Especially, emergency operation for treatment of a ruptured aneurysm has a low life-saving rate, and operation on dissecting aortic aneurysms is difficult and has a high death rate.

The present invention has been accomplished to solve the above-mentioned problems encountered in the prior art. The primary object of the invention is to provide an appliance which is collapsible for insertion into human organs such as a blood vessel and can be brought to an affected or constricted part thereof, where the appliance is released so as to be expanded and implanted there without fail. Another object of the invention is to make it easy to collapse the appliance and introduce it into a catheter for insertion into a human organ. A third object of the invention is to provide a device capable of collapsing the appliance for insertion into human organs with ease and accuracy.

DISCLOSURE OF THE INVENTION

The appliance collapsible for insertion into human organs and capable of resilient restoration in accordance with the invention is characterized by that a pair of foldable, elastic end wire rings are provided at opposite ends; that a plurality of foldable, elastic connecting wire rings having a generally circular shape when no external force is applied thereto are provided to bridge the opposite end wire rings and fixed thereto; and that a plurality of intermediate wire rings are provided between the opposite end wire rings so as to keep the connecting wire rings resiliently transformed to a generally elliptical shape.

A plurality of loops for pull strings to be passed through may be provided at a plurality of points which divide the circumference of each of the opposite end wire rings.

The appliance for insertion into human organs in accordance with the invention is characterized by that a pair of foldable, elastic end wire rings are provided at the opposite ends of a tube made of cloth or a sheet of flexible material; that a plurality of foldable, elastic connecting wire rings having a generally circular shape when no external force is applied thereto are provided to bridge the opposite end wire rings and fixed thereto; and that a plurality of intermediate wire rings are provided between the opposite end wire rings so as to keep the connecting wire rings resiliently transformed to a generally elliptical shape.

The appliance collapsible for insertion into human organs and capable of resilient restoration is characterized by that a pair of foldable, elastic wire rings are provided at the opposite ends of a tube made of cloth or a sheet of flexible material, and loops for a pull string to be passed through are provided at a plurality of points which divide the circumference of each of the end wire rings.

The device for collapsing the appliance for insertion into human organs in accordance with the invention is characterized by comprising a funnelled tube which is provided at its rear end with an inlet opening of a large diameter for the appliance to be inserted through from the front end thereof, and which has an intermediate tubular portion gradually reduced in diameter, and which terminates in a connecting tube having a smaller diameter than that of the appliance and adapted to be fitted into the rear end of a catheter.

In accordance with the invention, when the appliance, which comprises a pair of foldable, elastic end wire rings provided at opposite ends; a plurality of foldable, elastic connecting wire rings having a generally circular shape when no external force is applied thereto and adapted to bridge the opposite end wire rings and fixed thereto; and a plurality of intermediate wire rings provided between the opposite end wire rings so as to keep the connecting wire rings resiliently transformed to a generally elliptical shape, is inserted into a human organ, the foldable, elastic end wire rings, the intermediate wire rings and the connecting wire rings are folded thereby to collapse the appliance, which is inserted into a catheter, and the appliance is released at an objective position in the human organ, whereupon the resilient restoring forces of the end wire rings, the intermediate wire rings and the connecting wire rings restore the appliance to it sorignal tubular shape.

When the artificial body vessel comprising foldable, elastic end wire rings, intermediate wire rings and connecting wire rings is collapsed and inserted into a catheter, and released therefrom at an objective position (affected portion) in, say, a blood vessel, the resilient restoring forces of the end wire rings, the intermediate wire rings, the connecting wire rings cause the artificial body vessel to be restored to a tubular shape and pressed onto the inner wall of the blood vessel. Under the condition, the opposite end portions of the artificial body vessel are pressed onto the inner wall of the blood vessel, and the middle portion of the artificial body vessel prevents the blood vessel from being closed by an external force after implantation, and the resilient restoring force of the connecting wire rings helps to keep the whole shape of the artificial body vessel when restored.

By inserting and releasing the artificial body vessel in a constricted part of a human organ, it is possible to expand the constricted part by the artificial body vessel.

The appliance of the invention has an advantage that it can be brought to a desired position such as an affected part of a blood vessel in collapsed condition without a surgial operation, and be released at the position so as to be resiliently restored to the original tubular shape thereby to implant the appliance or expand a constricted part of a human organ.

The appliance provided at those points which divide the circumference of the end wire rings with loops for pull strings to be passed through can be inserted into a catheter directly or through a collapsing device, and transmitted through the catheter by pulling the pull strings. The work of collapsing and inserting the artificial body vessel into a catheter can be done easily and quickly.

When the appliance is introduced into the opening of an enlarged diameter of the funnelled tube and moved therethrough to the connecting end of the pipe, the wire rings are smoothly folded into a predetermined shape, so that the whole appliance can be collapsed into a predetermined shape with ease and accuracy.

BRIEF DESCRIPTION OF THE DRAWINGS

FIG. 3 is a perspective view of an example of the device for introducing a medium such as the above-mentioned artifical body vessel into a human body.

FIG. 4 is a perspective view showing the artificial body vessel through which the tube of the above-mentioned device is loosely inserted.

FIG. 5 is a perspective view showing the above-mentioned artificial body vessel and the tube of the above-mentioned device with a string to be passed through the loops on the artificial body vessel and wound about the wire within the tube.

FIG. 6 is a perspective view showing the above string wound about the wire.

FIG. 27 is a view showing a different manner of collapsing the artificial body vessel of the invention.

FIG. 28 is a perspective view showing the above artificial body vessel in collapsed condition.

FIG. 29 is a perspective view showing a still different manner of collapsing the artificial body vessel of the invention.

FIG. 35 is a perspective view of a different example of the above device.

BEST MODES OF EMBODYING THE INVENTION

The invention will be described in detail with reference to the embodiments thereof shown in the accompanying drawings.

The appliance to be inserted into a human organ can take the form of, for example, an artificial blood vessel or an artificial body vessel or a frame for expanding constricted parts of human organs.

An artificial blood vessel 7 will be described below as an example of the appliance to be inserted into a human organ.

Figure 1:
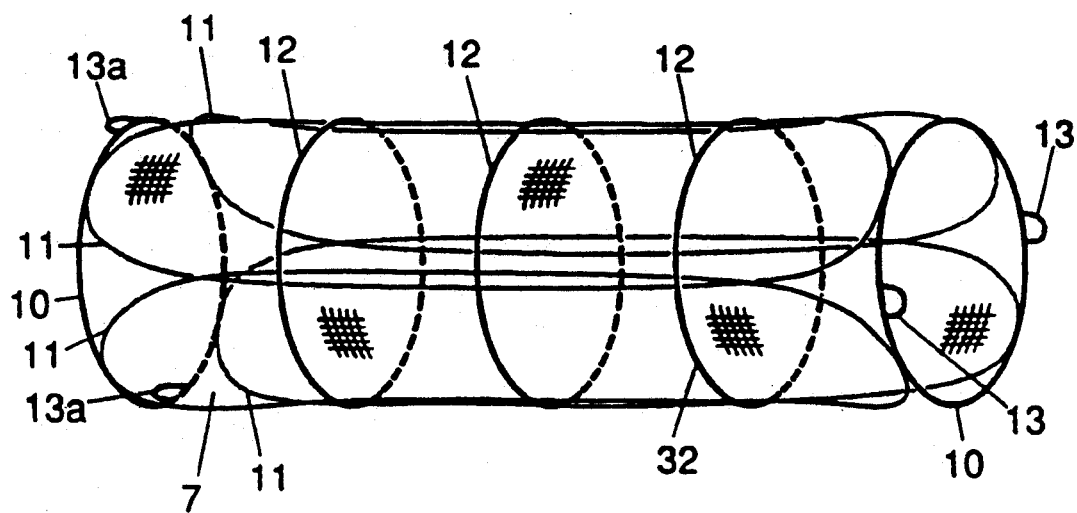
FIG. 1 is a perspective view of an artificial body vessel in accordance with the invention.
Figure 2:
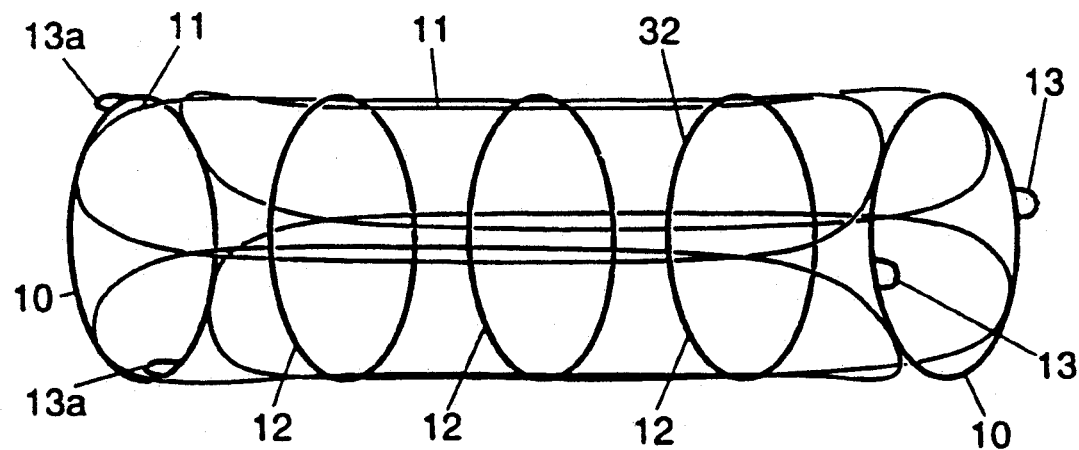
FIG. 2 is a perspective view of a frame included in the artrificial body vessel.

As shown in FIG. 1, the artificial blood vessel 7 is composed of a flexible tubular member made of cloth, film or the like, with a frame 32 for keeping the tubular shape. As shown in FIG. 2, the frame 32 has a three-dimentional construction comprising a pair of end wire rings 10 fixed to the opposite ends of the artificial blood vessel 7 by thread or adhesive, a plurality of connecting oblong wire rings 11 bridging the opposite end wire rings 10 and a plurality of intermediate wire rings 12 provided between the opposite end wire rings 10. The connecting wire rings 11 are made of wires of elastic material having a generally circular shape when no external force is applied thereto. As shown in FIG. 2, the connecting wire rings 11 are arranged between the opposite end wire rings 10 circumferentially thereof and fixed thereto. The elastic intermediate wire rings 12 are arranged between the opposite end wire rings 10. The intermediate wire rings 12 are partially fixed to the artificial blood vessel 7. Some of the intermediate wire rings 12 (in this embodiment, the two intermediate wire rings 12 adjacent the opposite end wire rings 10) are positioned outside the connecting wire rings 11 bridging the end wire rings 10 so as to transform their original circular shape into an elliptical shape as shown in FIGS. 1 and 2 thereby to cause the connecting wire rings to store a resilient restoring force to return to their original circular shape. This resilient force acts as a spring force to restore the collapsed artificial blood vessel 7 to its original tubular shape. The original shape of the connecting wire rings 11 without any external force applied thereto is not limited to a strictly circular shape, but it may also be elliptical. In the latter case, the originally elliptical connecting wire rings 11 are previously deformed into a more elliptical shape by application of an external force thereto and then disposed between the opposite end wire rings 10. In the embodiment shown in FIGS. 1 and 2, the middle one of the three intermediate rings 12 is positioned inside the oblong connecting wire rings 11 so as to prevent the connecting wire rings 11 from being pushed into the artificial blood vessel 7.

The connecting wire rings 11 and the intermediate wire rings 12 are not fixed to each other in order that the appliance may be smoothly collapsed without the connecting wire rings 11 and the intermediate wire rings 12 interfering with each other. It is possible to fix some of the intermediate wire rings 12 partially to the connecting wire rings 11. The connecting wire rings 11 may be interconnected to each other at one or more points thereof. That one of the intermediate wire rings 12 which is disposed outside the connecting wire rings 11 functions to transform the connecting wire rings 11 to a generally elliptical shape as mentioned above. On the other hand, the connecting wire rings 11 resiliently transformed to an elliptical shape continuously exerts on the intermediate rings 12 a force to expand thereby to help the intermediate wire rings 12 that have been folded to restore their original circular shape. In the illustrated embodiment, the connecting wire rings 11 are not directly fixed to the artificial blood vessel 7, but parts of them may be fixed to the artificial blood vessel 7, if necessary.

The above-mentioned end wire rings 10 are made of a flexible material which has a high resilent restoring force, such as Ti-Ni alloy. Of cource the material is not limited to Ti-Ni alloy. The wires of the alloy are hard to weld, but the annular shape makes it easy to connect the members to each other by a string, so that it becomes easy to assemble the component members. The diameters of the end wire rings 10, the connecting wire rings 11 and the intermediate wire rings 12 are set to 20 mm to 39 mm in accordance with that of the artificial blood vessel 7. The length of the artificial blood vessel 7 is determined in accordance with the length of the portion of an organ at which the artificial blood vessel is to be implanted.

A pair of loops 13 made of thread at two opposite positions of the circumference of the opening at one of the opposite ends of the artificial bool vessel 7 to which the end wire rings 10 are fixed. If necessary, similar loops 13a made of thread may also be provided at two opposite positions of the circumference of the opening at the opposite end of the artificial blood vessel 7. In this case, the position of the loops 13a are circumferentially displaced 90° from the loops 13.

The artificial blood vessel 7 of the above-mentioned construction is introduced into a human body vessel by means of a device as shown in FIG. 3 for introducing a medium into a human body esssel. The device comprises a flexible metallic tube 2 formed with a side window 1 adjacent the front end thereof, a string 4 having one end fixed to the tube 2 adjacent the side window 1, and a wire 3 slidably inserted into the tube 2.

By using the device of the above-mentioned construction for introducing a medium into a human body vessel, the artificial blood vessel 7 of the invention is introduced into a target position (an affected part 26) of a blood vessel 9 which is part of a human body in the following manner.

Figure 24:
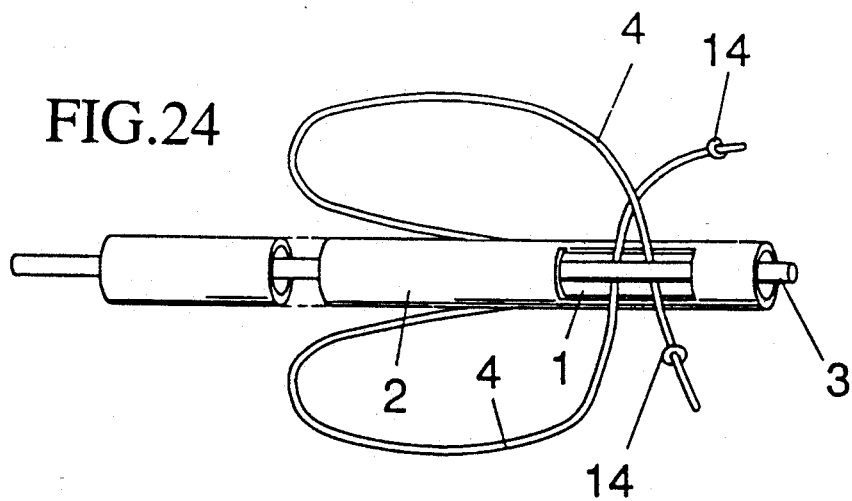
FIG. 24 is a perspective view of another example of the device for introducing the artificial body vessel of the invention into a human body.

The tube 2 is inserted through the artificial blood vessel 7 of the above-mentioned construction as shown in FIG. 4, and a string 4 is passed through the loops 13 provided at the front end of the artificial bood vessel 7 and wound about the wire 3 in a half, one or several turns at the side window 1 of the tube 2 as shown in FIG. 5 thereby to hold the artificial blood vessel 7 on the wire 3 inserted into the tube 2. In particular, by taking the front end portion of the wire 3 out of the side window 1, winding the string 4 about the wire 3, and then inserting the front end of the wire 3 into the tube 2, it is possible to easily wind the string 4 about the wire 3 at the side window 1. If the string 4 is formed with an enlarged portion such as a knot 14 as shown in FIG. 6, the string 4 is nipped between the edge of the side window 1 and the wire 3, so that the string 4 is held the more securely. A plurality of strings 4 may be provided as shown in FIG. 24.

With the artificial blood vessel 7 held on the tube 2 by the wire 3 in the above-mentioned manner, the tube 2 is inserted into a catether 8 as far as the target position (the affected part) 26 in the blood vessel 9. To this end, the tube 2 may be pushed directly into the catheter 8 through its rear end, and the artificial blood vessel 7 may be pulled by the string 4 thereby to collapse and introduce the vessel 7 into the catheter 8 while deforming and folding the wire ring 10 at the front end of the vessel 7. Alternatively, the artificial blood vessel 7 may be collapsed beforehand by using a collapsing device as shown in FIG. 7, so that the collapsed blood vessel is inserted into the catheter 8.

A method of collapsing the artificial blood vessel 7 beforehand by the collapsing device shown in FIG. 7 and inserting it into a catheter will now be described below.

Figure 7A:
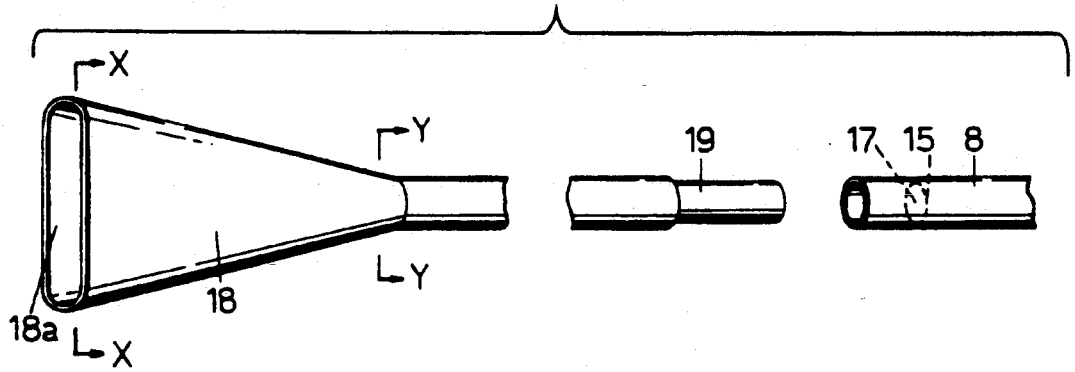
FIG. 7 shows a funnelled tube in one embodiment of the invention, A being a perspective view, B being a cross-sectional view along line X—X in A, and C being a cross-sectional view along line Y—Y in A.
Figure 7B:
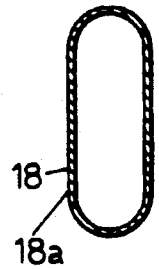
Figure 7C:

In FIG. 7, the reference numeral 18 designates a funnelled tube, the rear end portion of which is provided with an inlet opening 18a of an enlarged diameter, through which the tubular artificial blood vessel 7 is inserted into the tube 18 from the front end thereof. The tube 18 has a middle portion gradually reduced in diameter, and a front end portion made of a metallic tube circular in cross section and smaller in diameter than the artificial blood vessel 7 and formed into a connector 19 capable of being fitted into the rear end of the catheter 8 detachably therefrom. In FIG. 7, the reference numeral 15 designates a check valve provided in the rear end portion of the catheter 8 and made of elastic membrane, in which a normally closed hole 17 is formed. When the connector 19 composed of a metallic tube is inserted into the rear end portion of the catheter 8, the connector 19 pushes open the closed hole 17 in the elastic membrane so as to be inserted therethrough.

Figure 8:
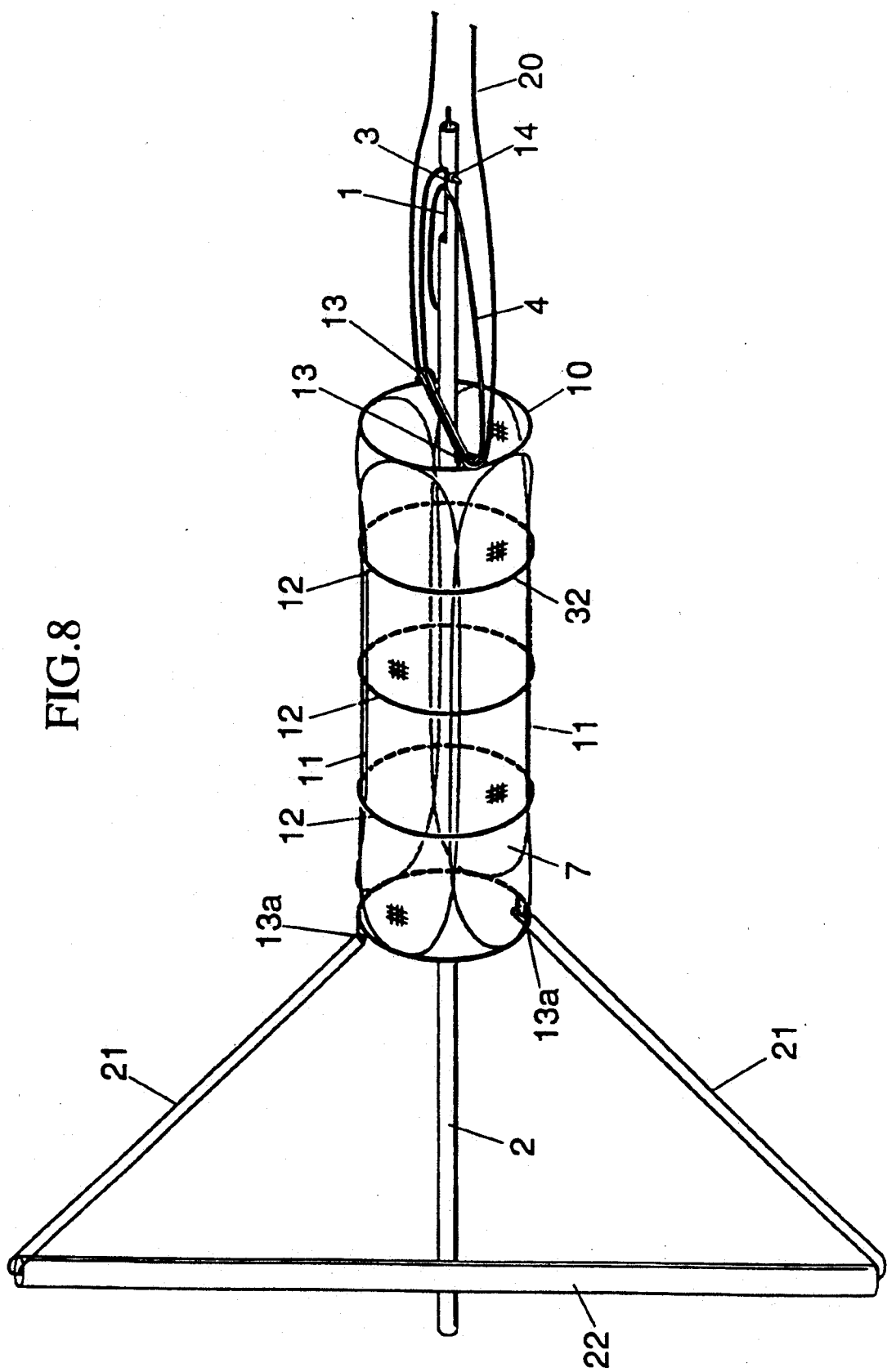
FIG. 8 is a perspective view showing a front pull string and rear pull strings passed through the above-mentioned front and rear loops.

In the illustrated embodiment, the funnelled tube 18 has an ellipticall cross-sectional shape, with the loops 13 being provided at two points bisecting the circumference of the front end wire ring 10. If loops 13 are provided at three points trisecting the circumference of the wire ring 10, the funnel of the tube 18 is made triangular in cross section. If loops 13 are provided at four points quadrisecting the circumference of the wire ring 10, the funnel of the tube 18 is made square in cross section. In the embodiment shown in FIG. 8, a front pull sring 20 is passed through the loops 13 provided at two opposite positions on the circumferential edge of the opening at the front end of the artificial blood vessel 7, and rear pull strings 21 are passed through the loops 13a provided at two opposite positions on the circumferential edge of the opening at the other end of the artificial blood vessel 7, with a rod-like grip 22 being fixed to the ends of the rear pull strings 21.

Figure 11:
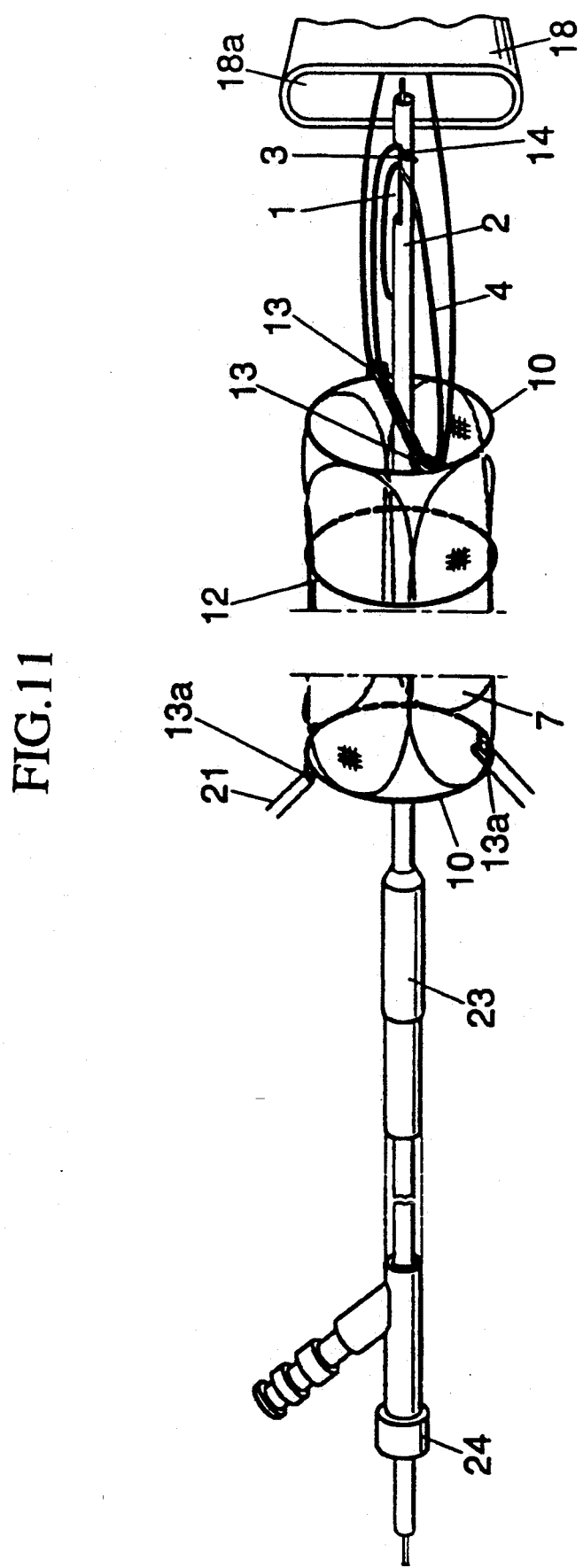
FIG. 11 is a perspective view showing the artificial body vessel before insertion into the above-mentioned funnelled tube.

Under the condition, a balloon catheter 23 is loosely fitted over the tube 2 of the introducing device so that the front end of the balloon catheter 23 is positioned about 2 to 3 cm apart from the rear end of the artificial blood vessel 7 as shown in FIG. 11. Then a fixing member 24 on the balloon catheter 23 is fastened to fix the catheter 23 to the tube 2 so that the catheter 23 can be moved together with the tube 2.

Figure 9:
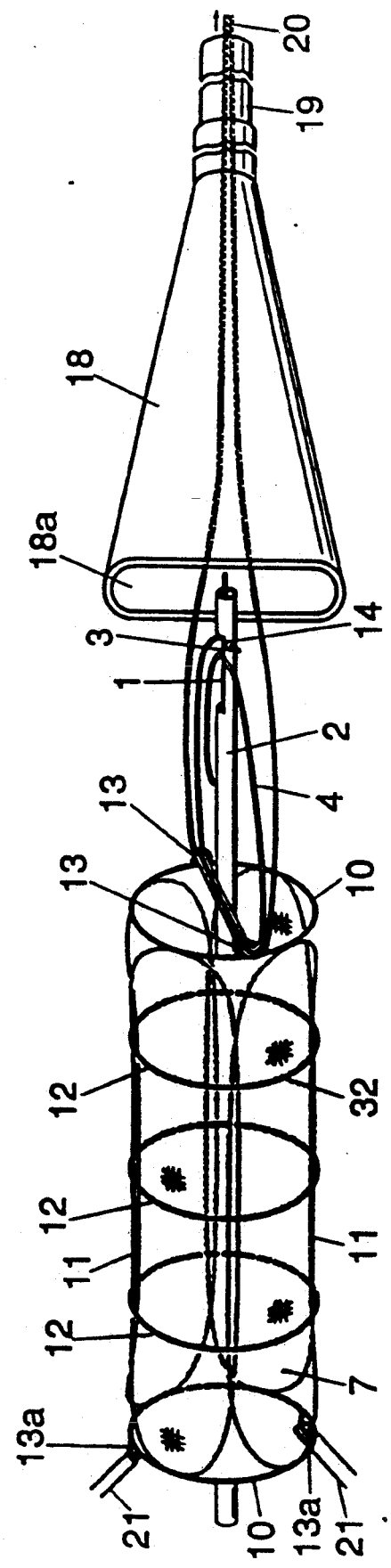
FIG. 9 is a perspective view showing an artificial body vessel before being inserted into the above-mentioned funnelled tube.
Figure 10:
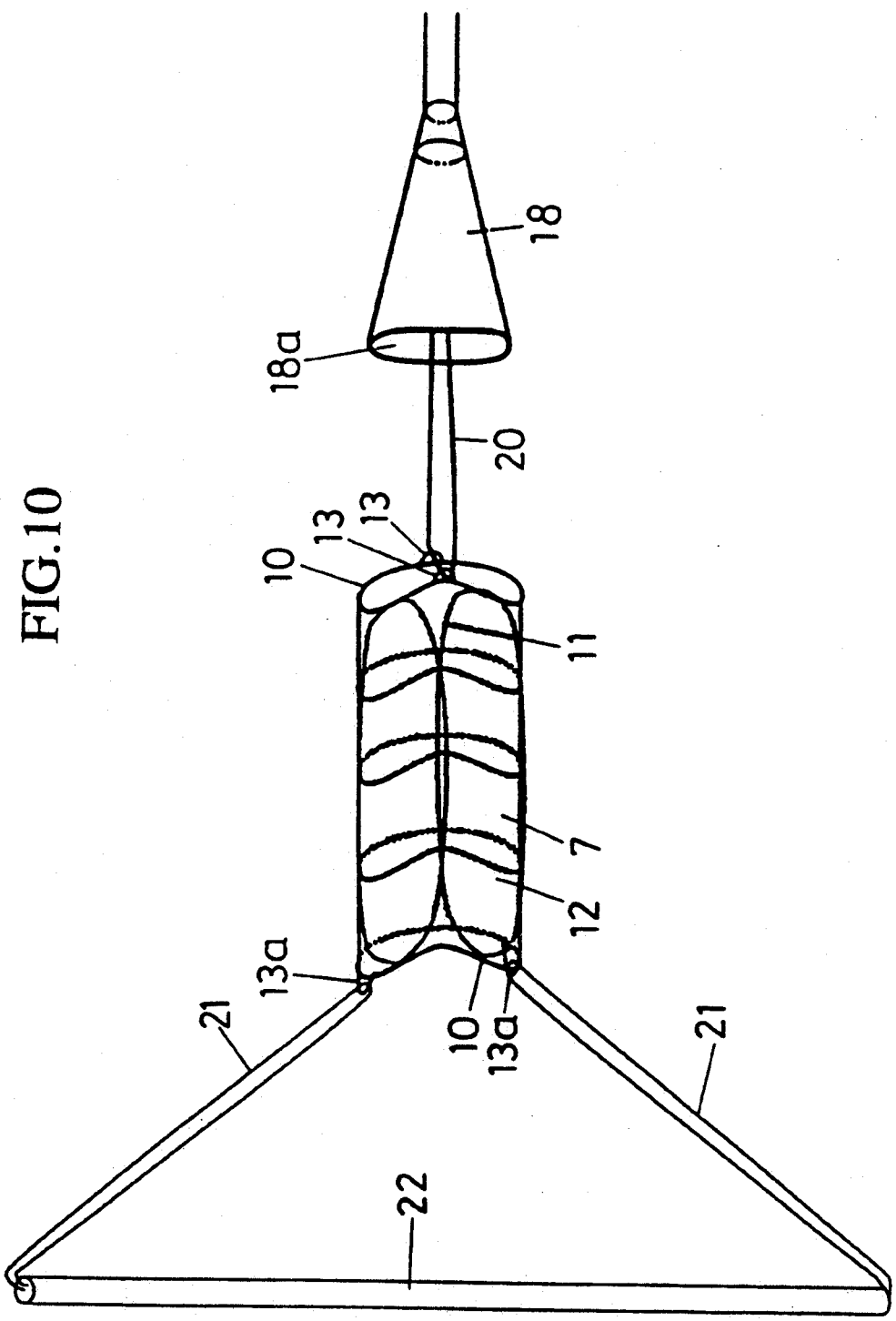
FIG. 10 is a perspective view showing the artificial body vessel immediately before being inserted into the funnelled tube, with the tube of the above-mentioned device not shown.

With the funnelled tube 18 disconnected from the catheter 8, the front pull string 20 is inserted through the rear end of the funnelled tube 18 and pulled forwardly from the front end of the connector tube 19, and at the same time the front end portion of the tube 2 is inserted a certain length into the funnelled tube 18 as shown in FIGS. 9 and 10. Under the condition, with a rearward pulling force applied to the rear end wire ring 10 of the artificial blood vessel 7 by the grip 22, the artificial blood vessel 7 is introduced into the funnelled tube 18 through the enlarged inlet opening 18a thereof by pulling forwardly the front pull string 20. Let it be assumed here for convenience of explanation that the circumference of the front end wire ring 10 is quadrisected by four imaginary points which (or the positions adjacent to which) will be referred to as the first, second, third and fourth points $41_1$, $42_1$, $43_1$ and $44_1$ respectively; that similarly the circumference of the rear end wire ring 10 is quadrisected by the first, second, third and fourth points $41_2$, $42_2$, $43_2$ and $44_2$ respectively; and that the loops 13 on the front end wire ring 10 are positioned at the first and third points $41_1$ and $43_1$ while the loops 13a on the rear end wire ring 10 are positioned at the second and fourth points $42_2$ and $44_2$. The artificial blood vessel 7 is so arranged with respect to the funnelled tube 18 that the line connecting the first and third points $41_1$ and $43_1$ on the front end wire ring 10 lies substantially along the short axis of the ellipse of the enlarged inlet opening 18a as shown in FIG. 7B while the line connecting the second and fourth points $42_1$ and $44_1$ lies along the long axis of the ellipse. In short, the artificial blood vessel 7 is set with respect to the funnelled tube 18 as shown in FIG. 10.

Figure 17A:
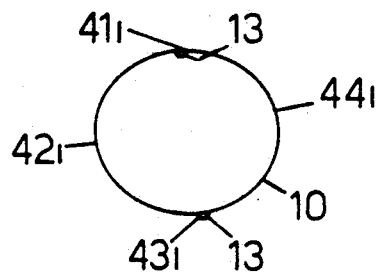
FIG. 17 shows the steps of folding the front end wire ring of the above-mentioned artificial body vessel.
Figure 17B:
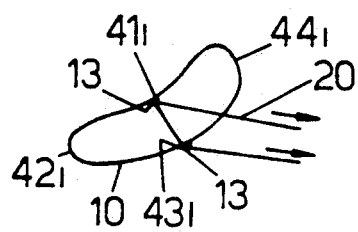
Figure 17C:
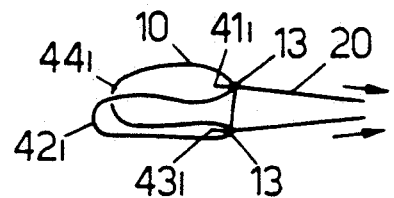

Under the condition, as the front pull string 20 is pulled, the first and third points $41_1$ and $43_1$, which are the two opposite points on the front end wire ring 10 of the artificial blood vessel 7 where the loops 13 are provided, are pulled by the front pull string 20, so that the front end wire ring 10 is collapsed flatly with the first and third points $41_1$ and $43_1$ where the loops 13 are provided approaching each other. Since the first and third points $41_1$ and $43_1$ are pulled ahead, the collapsed front end wire ring 10 is inserted into the funnelled tube 18 while being further collapsed, with the opposite second and fourth points $42_1$ and $44_1$ on the collapsed front end wire ring 10 being positioned rearwardly and approaching each other. In short, the front end wire ring 10 is transformed from the condition shown in FIG. 17A to the condition shown in FIG. 17B and thence to the condition shown in FIG. 17C, with the first and third points $41_1$ and $43_1$ forming forwardly directed peaks and the second and fourth points $42_1$ and $44_1$ forming the bottoms of forwardly directed valleys, so that the front end wire ring 10 as a whole takes a wavy shape.

Figure 18A:
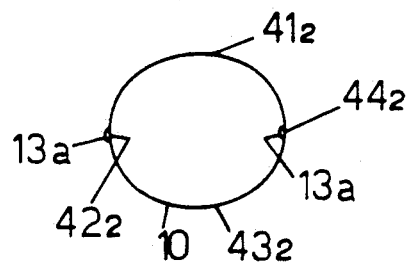
FIG. 18 shows the steps of folding the rear end wire ring of the artificial body vessel.
Figure 18B:
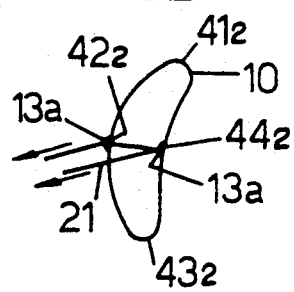
Figure 18C:
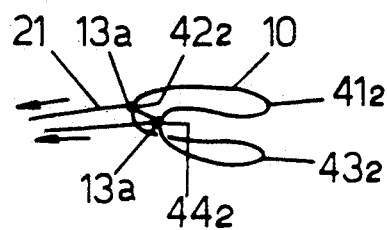

As the front pull string 20 is pulled further forwardly, with the rear pull strings 21 holding the rear end wire ring 10 at the opposite loops 13a (provided at the second and fourth points $42_2$ and $44_2$ of the rear end wire ring 10), the rear end wire ring 10 is pulled rearwardly at the loops 13a. At the same time, since the front end of the artificial blood vessel 7 is pulled forwardly by the above-mentiolned front pull string 20, the rear end wire ring 10 is collapsed flatly and inserted into the funnelled tube 18, with the first and third points $41_2$ and $43_2$ advancing ahead while approaching each other, and the second and fourth points $42_2$ and $44_2$ being positioned rearwardly and approaching each other. In short, the rear end wire ring 10 is transformed from the condition shown in FIG. 18A to the condition shown in FIG. 18B and thence to the condition shown in FIG. 18C, with the second and fourth points $42_2$ and $44_2$ forming rearwardly directed peaks, and the first and third points $41_2$ and $43_2$ forming the bottoms of rearwardly directed valleys, so that the rear end wire ring 10 as a whole takes a wavy shape.

Figure 19A:
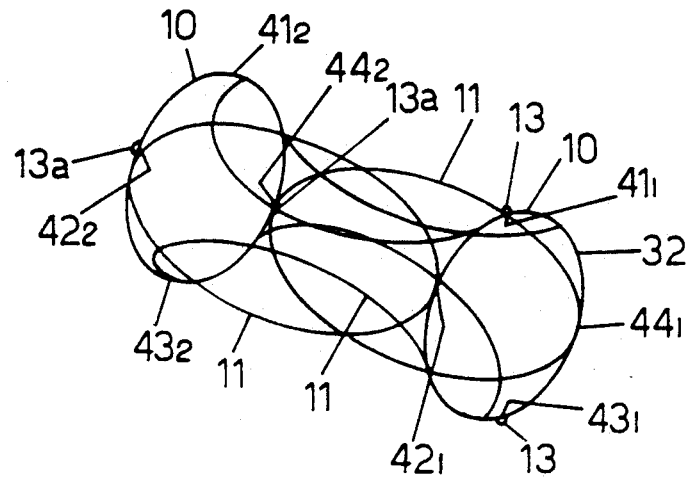
FIG. 19 shows the steps of folding the front and rear end wire rings and the connecting wire rings of the artificial body vessel, A showing a condition before folding, and B showing a condition after folding.
Figure 19B:
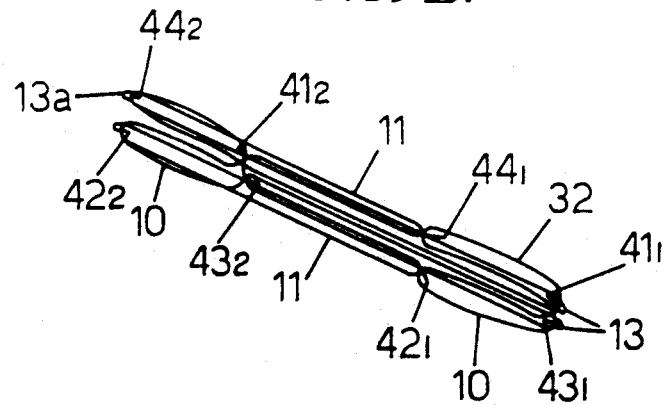
Figure 20:
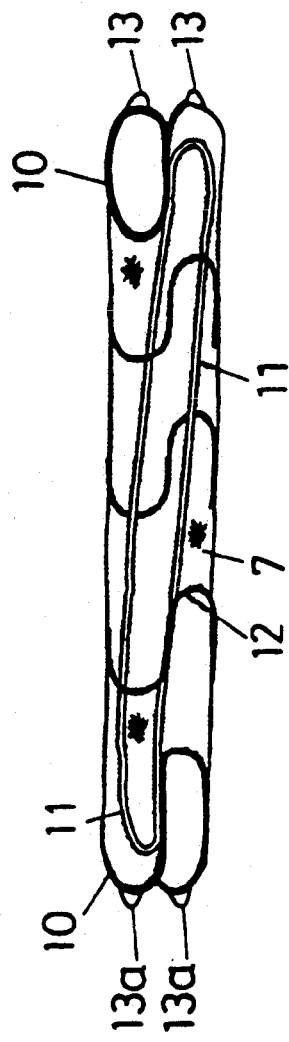
FIG. 20 is a perspective view showing the above-mentioned artificial body vessel collapsed.

FIGS. 19A and 19B show the relation between the front and rear end wire rings 10 and the connecting wire rings 11 of the artificial blood vessel 7 at different steps of collapsing the vessel 7 in the above-mentioned manner. (For simplicity of illustration, the intermediate rings 12 are not shown in the figures.) In short, the rings 10 and 11 are folded as shown in FIGS. 19A and 19B. Under the folded condition shown in FIG. 19B, the connecting wire rings 11 extend almost linearly and will not be loosened. FIG. 20 shows the artificial blood vessel 7 collapsed in the above-mentioned manner. After the artificial blood vessel 7 has been introduced through the enlarged inlet 18a of the funnelled tube 18 into the connecting tube 19 while being collapsed in the above-mentioned manner, the front and rear pull strings 20 and 21 are untied and pulled at their ends so as to be withdrawn from the loops 13 and 13a.

Figure 12:
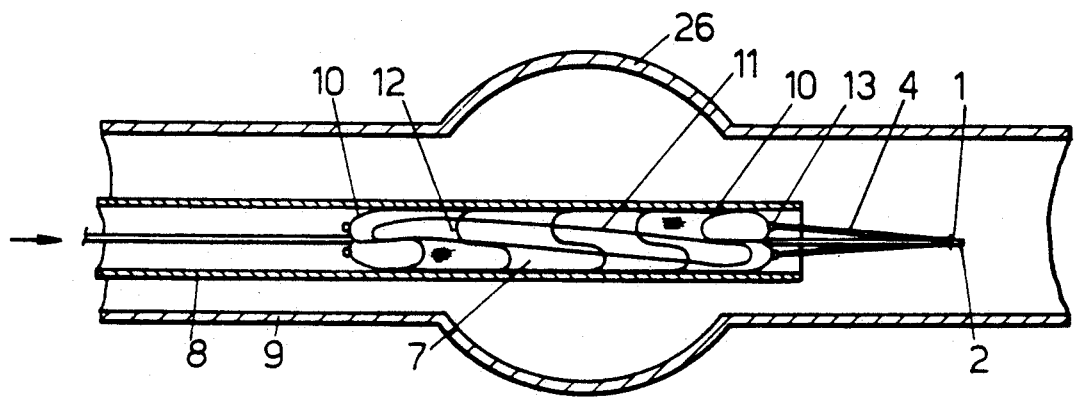
FIG. 12 is a cross-sectional view showing the tube of the above-mentioned device and the artificial body vessel in a catheter inserted into a blood vessel.
Figure 13:
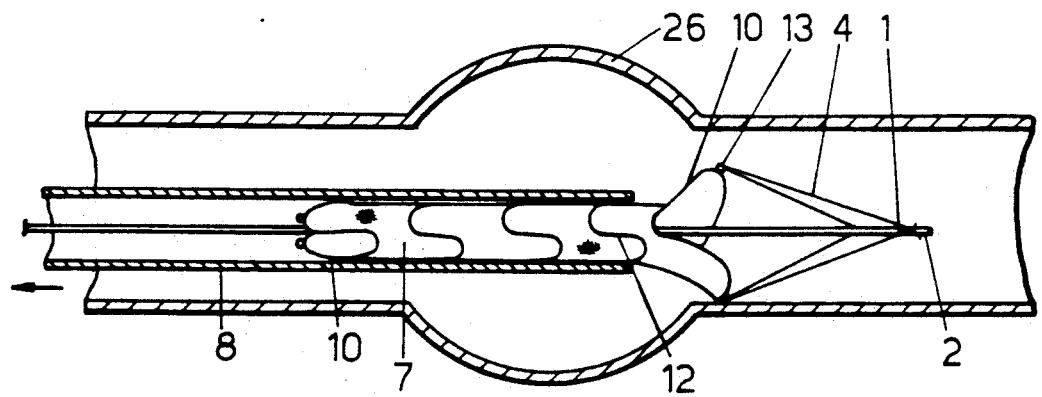
FIG. 13 is a cross-sectional view showing the catheter being pulled out leaving the tube of the above-mentioned device.
Figure 14A:
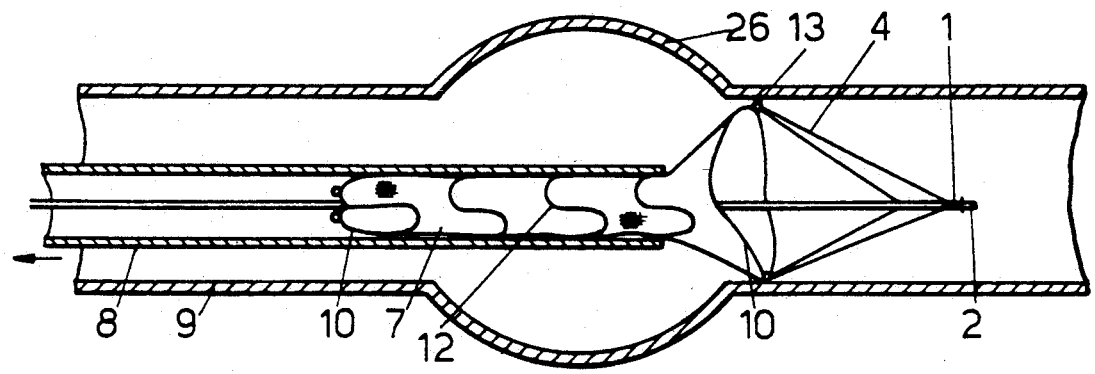
FIG. 14 shows the above-mentioned catheter being pulled, A being a cross-sectional view showing the catheter pulled out midway, and B being a cross-sectional view showing the catheter completely pulled out.
Figure 14B:
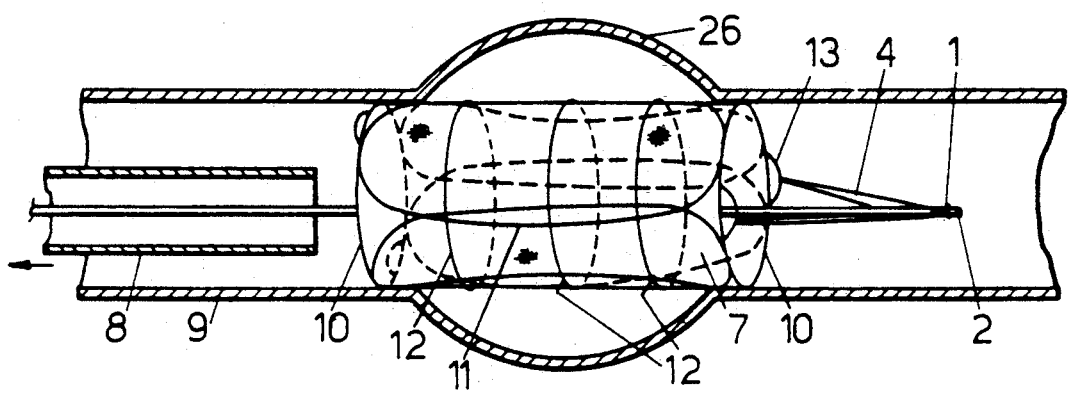

On the other hand, the catheter 8 was previously inserted through, say, the coxal artery adjacent the groin into an aorta 9 as far as the front end of the catheter was positioned a little beyond the affected part such as an aneurysm 26 of the aorta. Then the metallic connecting end 19 of the funnelled tube 18 is inserted through the hole 17, that is, the check valve 16 in the elastic membrane at the rear end of the catheter 8, and the tube 2 of the introducing device containing the wire 3 is inserted into the catheter 8 as far as the front end of the tube 2 containing the wire 3 is positioned adjacent the front end of the catheter 8 as shown in FIG. 12 thereby to place the artificial blood vessel 7 held by the wire 3 at the objective position in the catheter 8. Then, as the catheter 8 is withdrawn as shown in FIGS. 13 and 14, with the tube 2 holding the collapsed artificial blood vessel 7 by the wire 3 left at the objective position, the collapsed artificial blood vessel 7 in the catheter 8 is released into the blood vessel 9 while expanding gradually from the front end as shown in FIGS. 13, 14A and 14B. The released artificial blood vessel 7 is restored to its original tubular contour by the resiliency of the end wire rings 10 and the connecting wire rings 10 and urged against the inner wall of the blood vessel 9. If the released artificial blood vessel 7 is displaced from the proper position, the tube 2 is moved forwardly or rearwardly to adjust the position of the artificial blood vessel 7.

Figure 15:
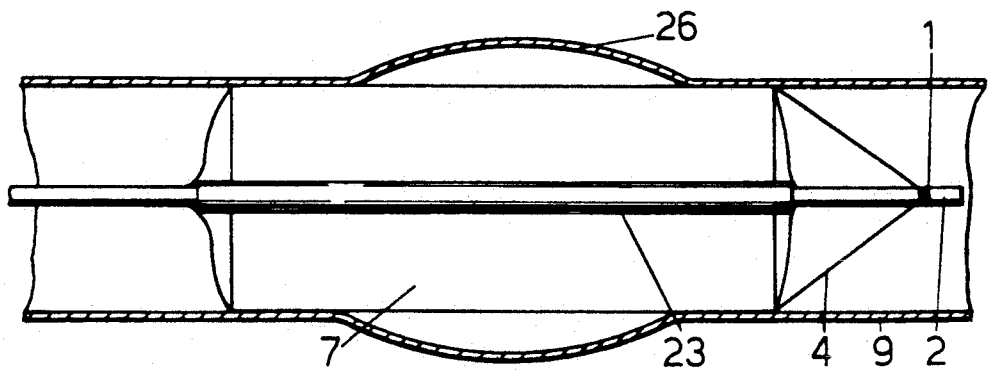
FIG. 15 is a cross-sectional view showing a balloon catheter moved into the artificial body vessel.

Then the fixig member 24 is loosened to disconnect the ballon catheter 23 from the tube 2, and the balloon catheter 23 is advanced along the tube 2 into the artificial blood vessel 7 as far as the front end of the balloon catheter 23 reaches the front end of the artificial blood vessel 7 as shown in FIG. 15, whereupon the balloon is inflated as shown by dash-and-dot lines in FIG. 15 thereby to expand the artificial blood vessel 7 completely and securely fix it onto the inner wall of the blood vessel 9.

Figure 16:
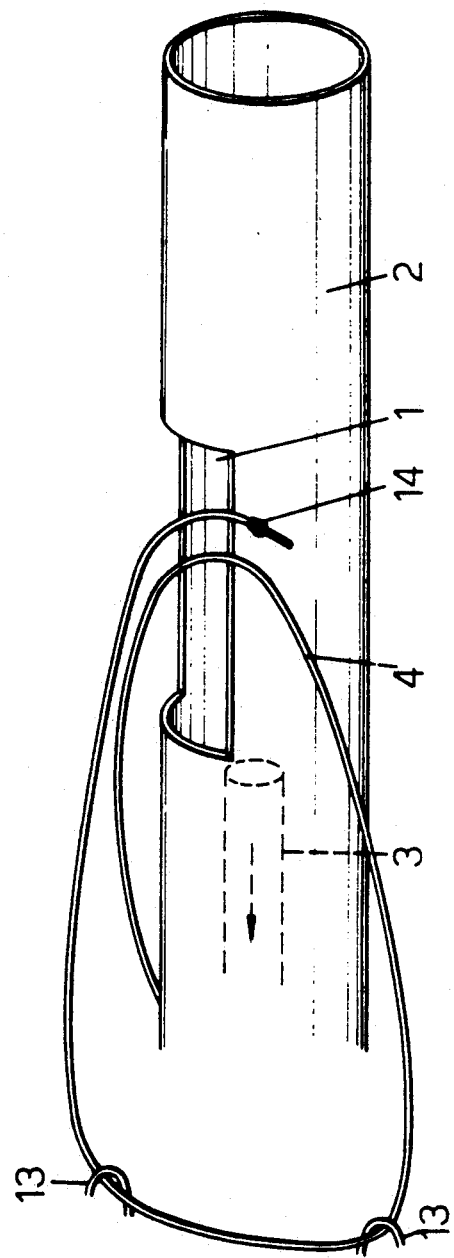
FIG. 16 is an enlarged perspective view showing the string released from the wire by withdrawing the wire relative to the tube of the above-mentioned device.

After the artificial blood vessel 7 has been fixed, the balloon is deflated and the balloon catheter 23 is pulled out. Then it is confirmed that the artificial blood vessel 7 has been fixed onto the inner wall of the blood vessel 9, and the wire 3 is pulled out of the tube 2. As the front end of the wire 3 passes the rear edge of the side window 1 of the tube 2 as shown in FIG. 16, the string 4 that has been caught by the wire 3 at the window 1 is released from the wire 3. Under the condition, as the tube 2 is pulled out, the string 4 slips out of the loops 13 of the artificial blood vessel 7, and the tube 2 comes out leaving the artificial blood vessel 7 in place in the blood vessel 9.

In the above embodiment, the ballon catheter 23 is used. It is possible to make the artificial blood vessel 7 contact the inner wall of the blood vessel 9 by the resiliency of the artificial blood vessel 7 alone without using a balloon catheter.

Figure 21:
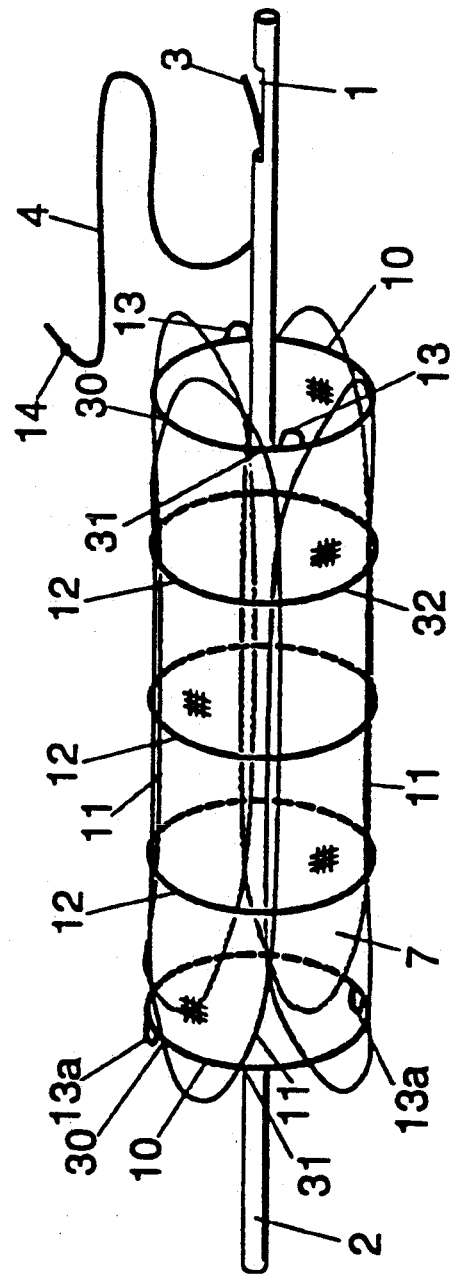
FIG. 21 is a perspective view of another embodiment of the invention.

Another example of the artificial blood vessel 7 of the invention will be described with reference to FIG. 21. In this embodiment, the opposite end portions of the connecting wire rings 11 project outwardly along the axis of the artificial blood vessel 7 beyond the front and rear end wire rings 10 thereof. In this arrangement, each of the connecting wire rings 11 is fixed to each of the front and rear end wire rings 10 at two points 30 and 31, so that when the wire rings 10 once folded are restored to the original shape, the resiliency of the connecting wire rings 11 to return to their circular shape acts on the end wire rings 10 to help them to return to their original circular shape. The projection of the connecting wire rings 11 beyond the opposite ends of the artificial blood vessel 7 prevents the bordering portions of the blood vessel 9 and the implanted artificial blood vessel 7 from becoming steped thereby to help the inner wall of the artificial blood vessel 7 to join the inner wall of the blood vessel 9 smoothly and evenly.

Figure 22:
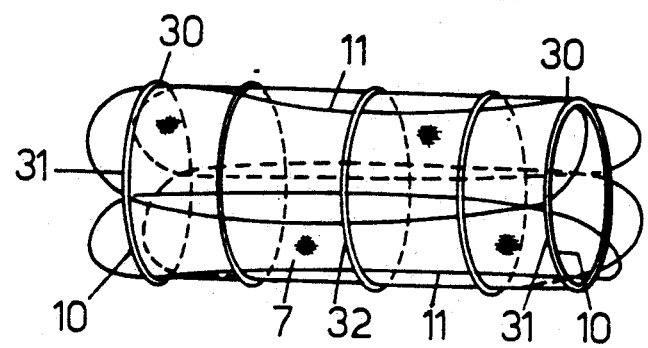
FIGS. 22A and 22B show different embodiments of the invention in perspective view.
Figure 22:
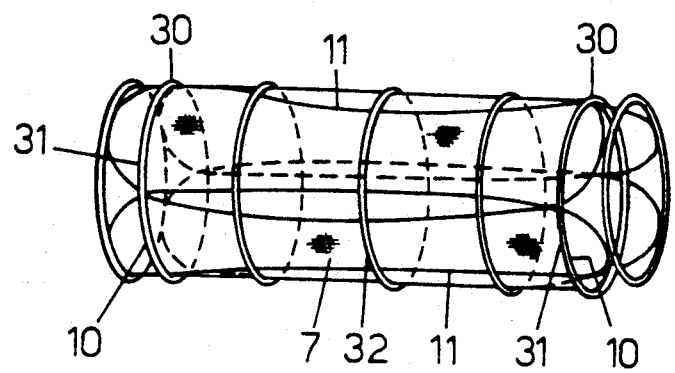

As shown in FIGS. 22A and 22B, the connecting wire rings 11 may be fixed to the end wire rings 10 at the crossing points of each adjacent two of the connecting wire rings 11.

As shown in FIG. 22B, an additional pair of wire rings 10a may be fixed to the axially outwardly projecting ends of the connecting wire rings 11 beyond the opposite end wire rings 10. The added rings 10a not only prevent the projecting ends of the connecting wire rings 11 from scratching the inner wall surface of the blood vessel 9, but also help the opposite ends of the connecting wire rings 11 to expand into close contact with the inner wall surface of the blood vessel 9 thereby to prevent the implanted artifiical vessel 7 from being carried away downstream by blood flow.

Figure 23:
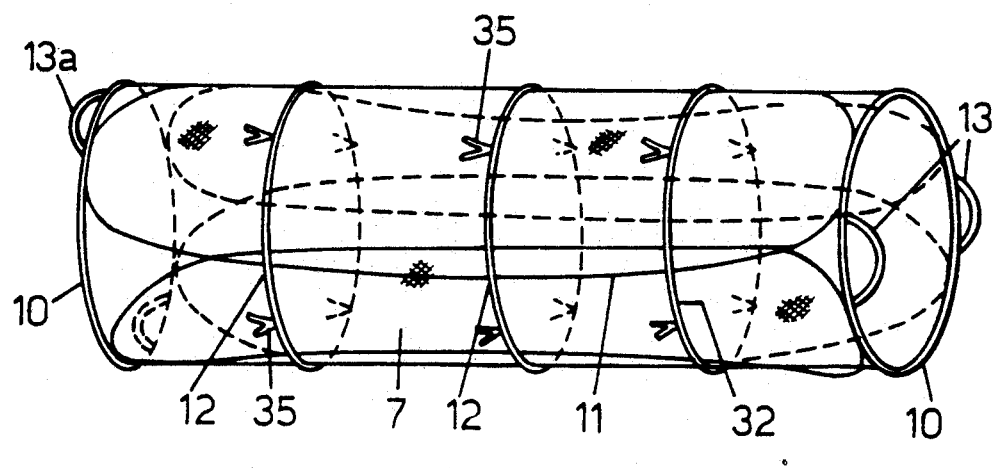
FIG. 23 is a perspective view of a further different embodiment of the invention.

As shown in FIG. 23, projections 35 may be formed on the exterior wall surface of the artificial blood vessel 7. The projections 35 may be more or less V-shaped as shown in FIG. 23 or wart-like, or have a pointed end, or take various other forms. The projections may be made of wire, hard thread, rubber or any other suitable materials. The projections 35 may be formed on the end wire rings 10 or the connecting wire rings 11, or on the outer surface of the cloth or film constituting the body of the artificial blood vessel 7. The projections 35 may stand perpendicular to the exterior surface of the artificial blood vessel 7, or inclined rearwardly. The projectings 35 provided on the exterior surface of the artificial blood vessel 7 are pushed into the inner wall of the blood vessel 9 and provide frictional resistance to prevent the artificial blood vessel 7 from being carried away downstream by flood flow.

In the above-mentioned embodiments, the end wire rings 10, the connecting wire rings 11 and the intermediate wire rings 12 are arranged outside the cloth tube of the artificial blood vessel 7. They may be arranged inside the cloth tube.

Figure 25:
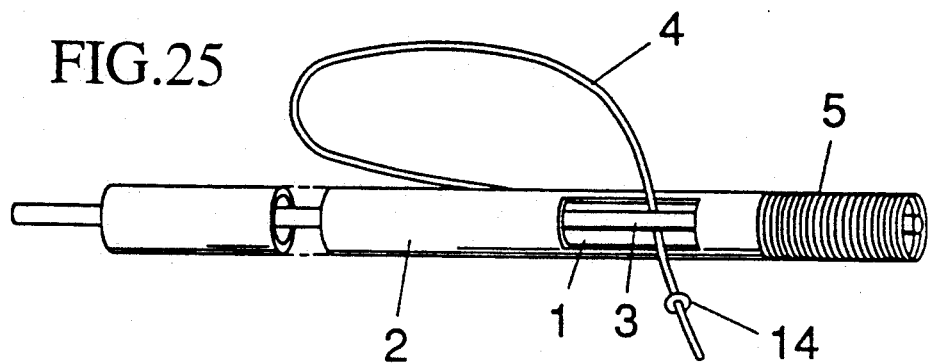
FIG. 25 is a perspective view of still another example of the above device.

FIG. 25 shows another example of the device for introducing a medium such as the artificial blood vessel 7 into a human body. In this example, the tube 2 is provided at the front end thereof with a soft, flexible guide tube 5 comprising a coil made of soft metal or synthetic resin such as polyethylene, or a tube made of soft synthetic resin or rubber. The soft, flexible tube 5 provided on the front end of the tube 2 is intended to prevent the tube 2 from injuring the inner wall of the blood vessel 9.

Figure 26:
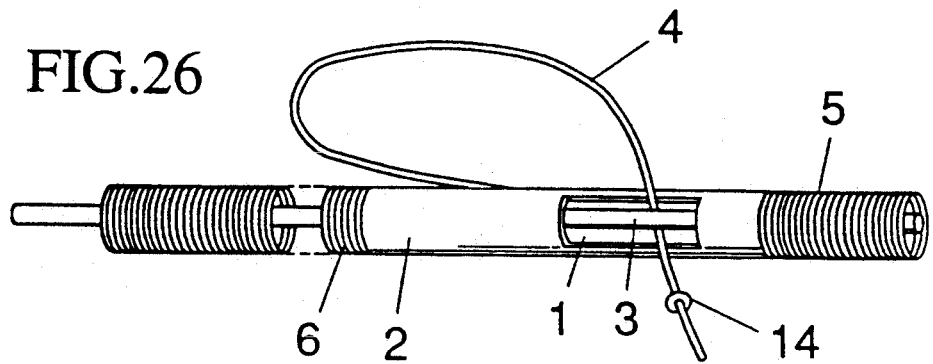
FIG. 26 is a perspective view of a different example of the above device.

FIG. 26 shows a third example of the device for introducing a medium into a human body. In this example, a short tube 2 is provided at its front end with a short guide tube 5 and at its rear end with a long guide tube 6. The short and long guide tubes 5 and 6 comprise a coil made of soft metal or synthetic resin such as polyethylene, or a tube made of soft synthetic resin or rubber. With the short and long flexible guide tubes 5 and 6 provided at the front and rear ends, respectively, of the tube 2, when the tube 2 is inserted into a meandrous blood vessel, the flexible front and rear guide tubes can move smoothly and easily along the meandrous blood vessel without danger of injuring the inner wall of the blood vessel 9.

In the above-mentioned embodiments, when the artificial blood vessel 7 is collapsed and inserted into the catheter 8, the front end wire ring 10 is folded at the first, second, third and fourth points $41_1$, $42_1$, $43_1$ and $44_1$ on the circumference of the ring, and the rear end wire ring 10 is folded at the first, second, third and fourth points $41_2$, $42_2$, $43_2$ and $44_2$.

In FIGS. 27 and 28, the front and rear end wire rings 10 have their respective circumferences divided into eight equal arcs by the first, second, third, fourth, fifth, sixth, seventh and eighth imaginary points $51_1$, $52_1$, $53_1$, $54_1$, $55_1$, $56_1$, $57_1$ and $58_1$, and $51_2$, $52_2$, $53_2$, $54_2$, $55_2$, $56_2$, $57_2$ and $58_2$, respectively. Loops 13 are provided on the front end wire ring 10 at the first, third, fifth and seventh points $51_1$, $53_1$, $55_1$ and $57_1$ while loops 13a are provided on the rear end wire rings 10a at the second, fourth, sixth and eighth points $52_2$, $54_2$, $56_2$ and $58_2$.

With the artificial blood vessel 7 having been set relative to a funnelled tube 18 provided with an enlarged inlet opening 18a square in cross section in such a manner that the first, third, fifth and seventh points $51_1$, $53_1$, $55_1$ and $57_1$ of the front end wire ring 10 are positioned about the middle of the four sides of the inlet opening 18a as shown in FIG. 27, as the front pull strings 20 are pulled, the first, third, fifth and seventh points $51_1$, $53_1$, $55_1$ and $57_1$ of the front end wire ring 10 where the loops 13 are provided are pulled by the strings 20 forwardly, so that the front end wire ring 10 is collapsed with the first, third, fifth and seventh points $51_1$, $53_1$, $55_1$ and $57_1$ advancing axially ahead while approaching each other. As the first, third, fifth and seventh points $51_1$, $53_1$, $55_1$ and $57_1$ are pulled ahead forwardly through the funnelled tube 18, the folded front end wire ring 10 is inserted into the tube 18, with the second, fourth, sixth and eighth points $52_1$, $54_1$, $56_1$ and $58_1$ on the front end wire ring 10 being positioned rearwardly and approaching each other. In other words, the front end wire ring 10 as a whole takes a wavy form, with the first, third, fifth and seventh points $51_1$, $53_1$, $55_1$ and $57_1$ on the front end wire ring 10 where the loops 13 are provided being positioned at forwardly directed peaks and the second, fourth, sixth and eighth points $52_1$, $54_1$, $56_1$ and $58_1$ being positioned at the bottoms of forwardly directed valleys.

Under the condition, as the front pull strings 20 are pulled further forwardly, with the rear end wire ring 10 being held by the rear pull strings 21 at the second, fourth, sixth and eighth points $52_1$, $54_1$, $56_1$ and $58_1$ where the loops 13a are provided, the rear end wire ring 10 is inserted into the funnelled tube 18 while being folded and deformed, with its first, third, fifth and seventh points $51_2$, $53_2$, $55_2$ and $57_2$ being pulled ahead into the funnelled tube 18 and approaching each other, and the second, fourth, sixth and eighth points $52_2$, $54_2$, $56_2$ and $58_2$ being positioned rearwardly and approaching each other. In other words, the rear end wire ring 10 as a whole takes a wavy form, with the second, fourth, sixth and eighth points $52_2$, $54_2$, $56_2$ and $58_2$ of the rear end wire ring where the loops 13a are provided being positioned at rearwardly directed peaks, and the first, third, fifth and seventh points $51_2$, $53_2$, $55_2$ and $57_2$ thereof being positioned at the bottoms of rearwardly directed valleys as shown in FIG. 28.

In FIG. 29, the front and rear end wire rings 10 have their circumferences divided into six equal arcs by six imaginary points, which (or the positions adjacent to which) will be referred to as the first, second, third, fourth, fifth and sixth points $61_1$, $62_1$, $63_1$, $64_1$, $65_1$ and $66_1$, and $61_2$, $62_2$, $63_2$, $64_2$, $65_2$ and $66_2$, respectively. Loops 13 are provided on the front end wire ring 10 at the first, third and fifth points $61_1$, $63_1$ and $65_1$ while loops 13a are provided on the rear end wire ring 10 at the second, fourth and sixth points $62_2$, $64_2$ and $66_2$.

With the artificial blood vessel 7 having been set relative to the funnelled tube 18 provided with an enlarged inlet opening 18a triangular in cross section in such a manner that the first, third and fifth points $61_1$, $63_1$ and $65_1$ of the front end wire ring 10 are positioned about the middle of the sides of the inlet 18a as shown in FIG. 29, as the front pull strings 20 are pulled, the first, third and fifth points $61_1$, $63_1$ and $65_1$ of the front end wire rings 10 where the loops 13 are provided are pulled by the front pull strings 20 forwardly, so that the front end wire ring 10 is collapsed, with the first, third and fifth points $61_1$, $63_1$ and $65_1$ advancing axially ahead while approaching each other. As the first, third and fifth points $61_1$, $63_1$ and $65_1$ are pulled ahead forwardly through the funnelled tube 18, the folded front end wire ring 10 is inserted into the tube 18, with the second, fourth and sixth points $62_1$, $64_1$ and $66_2$ being positioned rearwardly and approaching each other. In other words, the front end wire ring 10 as a whole takes a wavy form, with the first, third and fifth points $61_1$, $63_1$ and $65_1$ being positioned at forwardly directed peaks and the second, fourth and sixth points $62_1$, $64_1$ and $66_1$ being positioned at the bottoms of forwardly directed vallleys.

Under the condition, as the front pull strings 20 are pulled further forwardly, with the rear end wire ring 10 being held by the rear pull strings 20 at the second, fourth and sixth points $62_2$, $64_2$ and $66_2$ thereof where the loops 13a are provided, the rear end wire ring 10 is inserted into the funnelled tube 18 while being folded and deformed, with the first, third and fifth points $61_1$, $63_2$ and $65_2$ being pulled ahead forwardly into the tube 18, and the second, fourth and sixth points $62_2$, $64_2$ and $66_2$ being positioned rearwardly and approaching each other. In other words, the rear end wire ring 10 as a whole takes a wavy form, with the second, fourth and sixth points $62_2$, $64_2$ and $66_2$ where the loops 13a are provided being positioned at rearwardly directed peaks, and the first, third and fifth points $61_2$, $63_2$ and $65_2$ being positioned at the bottoms of rearwardly directed valleys.

In the above-mentioned embodiments, the front and rear end wire rings 10 have their circumferences divided into four, six and eigth equal arcs. They may be divided by ten or any other even number of points, at each of which a loop 13, 13a may be provided. In those cases, the loops 13, 13a are most preferably provided at those positions on the wire rings which correspond to the ends of the connecting wire ring 11, or at the middle positions on the end wire rings between the ends of each adjacent two of the connecting wire rings 11. With the loops 13 and 13a provided at such positions, it is possible to transform the wire rings 10 to a uniform wavy form. In the above embodiments, the connecting wire rings 11 are circular when no external force is applied to them. They may be elliptical when no external force is applied to them.

In the above embodiments, the appliance to be inserted into a human organ is used as, by way of example, an artificial blood vessel. It may be used as an aritificial body vessel for expanding constricted parts of human organs. In particular, the artificial body vessel 7 is inserted into a constricted part 26a of a human organ 9a as shown in FIG. 30 in the same manner as previously mentioned with respect to the artificial blood vessel, and then released at the position shown in FIG. 30, whereupon the constricted part 26a of the human organ 9a is expanded by the resiliency of the artificial body vessel of the same construction as the previously mentioned artificial blood vessel 7 as shown in FIG. 31.

Figure 30:
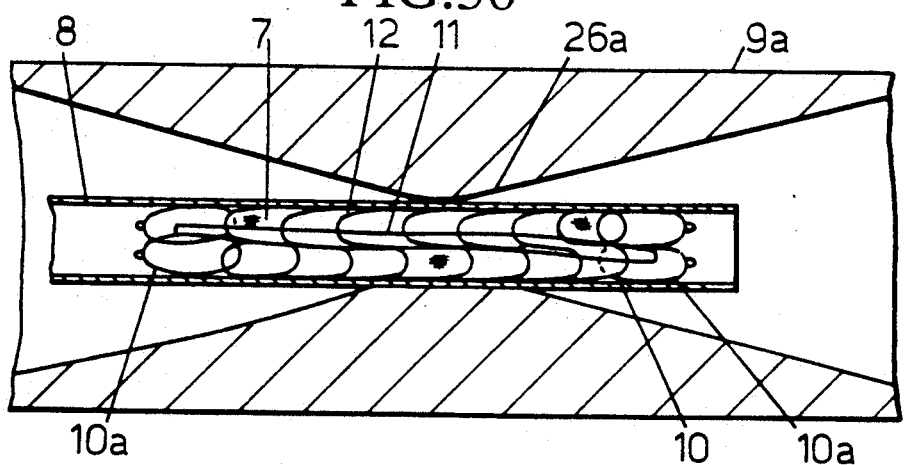
FIG. 30 is a perspective view showing the artificial body vessel of the invention inserted into a constricted portion.
Figure 31:
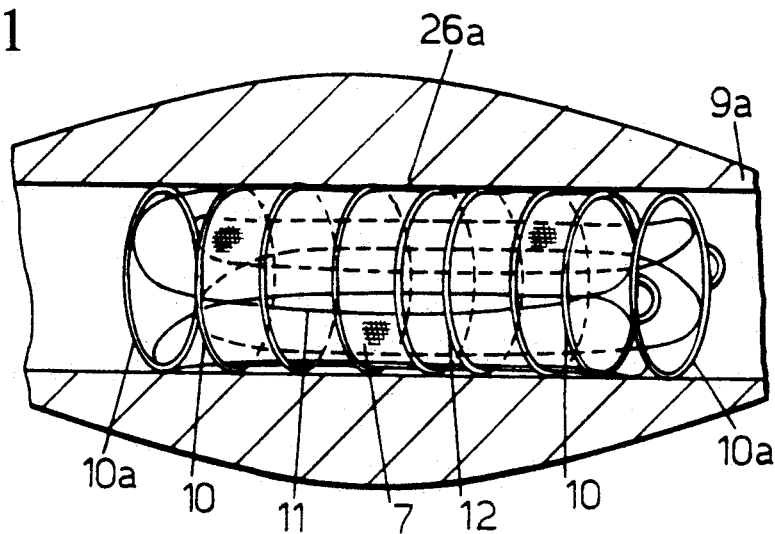
FIG. 31 is a perspective view showing the constricted portion having been expanded by the above artificial body vessel.

For expanding constricted parts of human organs not only the artificial body vessel 7 shown in FIGS. 30 and 31 but also those shown in FIGS. 21, 22A, 22B and 23 or those which have the same construction of any of the other embodiments of the invention may be used.

Figure 32:
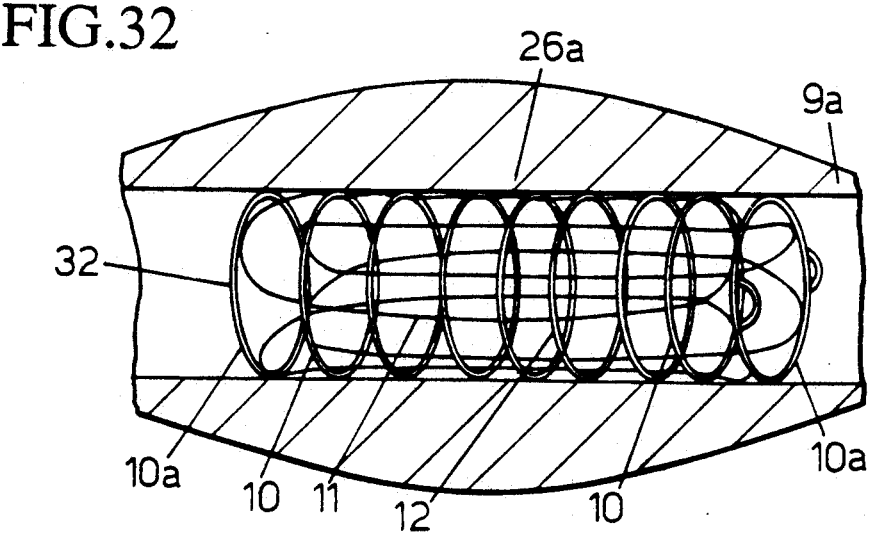
FIG. 32 is a perspective view showing the constricted portion having been expanded by the above frame.

FIG. 32 shows an example of the appliance for expanding a constricted part 26a of a human organ 9a, which comprises only a frame 32 without the tubular cloth or sheet used in the previously mentioned artificial blood vessel. In this case, only the frame 32 is inserted into the constricted part 26a of the human organ 9a in the same manner as previously mentioned, and then released in the constricted part 26a as shown in FIG. 32 to expand the part by the resilient restoring force of the frame 32. Not only the frame 32 of the construction shown in FIG. 32 but also those frames 32 of the artificial blood vessels 7 shown in FIGS. 21, 22A, 22B and 23 without the tubular cloth or sheet may be used as occasions demand.

Figure 33:
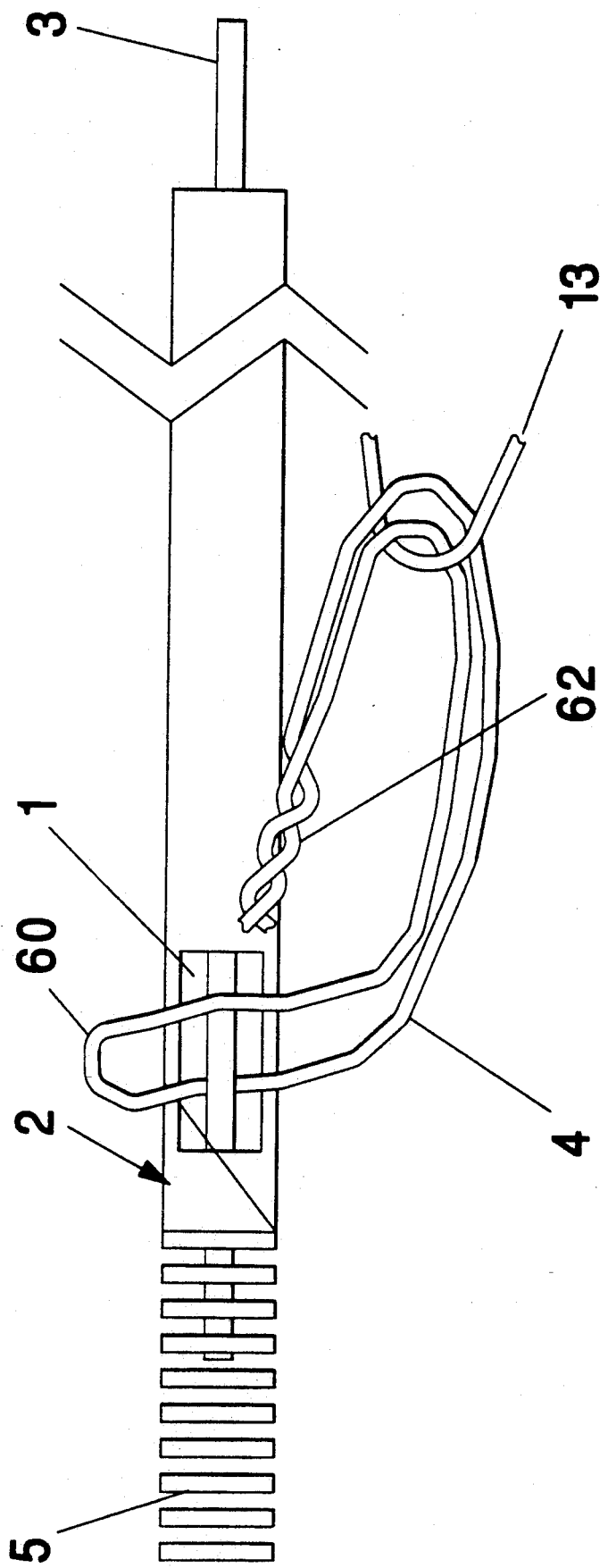
FIG. 33 is a perspective view of another example of the device for introducing the medium of the invention into a human body.

FIG. 33 shows an example of a device for introducing a medium, such as the artificial blood vessel 7, into a human body. In this embodiment, the device includes a tube 2 having a front end. The tube 2 is preferably fabricated to be a flexible metallic tube. The tube 2 is formed with a side window 1. The side window 1 is adjacent the front end of tube 2. The tube 2 is intended to be inserted through the medium and into a human body. The device includes a wire 3 which is slidably inserted through the tube 2, and through the front end of the tube, so as to extend along the side window 1 of the tube 2. The device includes at least one string 4 having a first end fixed to the tube 2 adjacent the side window 1. The at least one string 4 is arranged so as to be passed through the medium and wound around wire 3 where the wire 3 extends along the side window 1 of the tube 2. In this embodiment, the at least one string has a second end which is fixed to tube 2 adjacent the side window 1 so as to form a loop 60 through which the wire 3 is passed. The first end of the string and the second end of the string can be twisted together to form a single twisted terminal end 62. It is not necessary that the first end of the string 4 and the second end of string 4 be twisted together to form a single twisted terminal end 62. In this embodiment, the medium has a front opening provided with at least one loop 13 through which the string 4 is passed. The device includes a flexible guide tube 5 located at the front end of the tube 2. The guide tube 5 can be a soft flexible coil spring made of soft metal or synthetic resin such as polyethylene, or a tube made of soft synthetic resin or rubber. The soft, flexible tube 5 provided on the front end of the tube 2 is intended to prevent the tube 2 from injuring the inner wall of the blood vessel 9.

Figure 34:
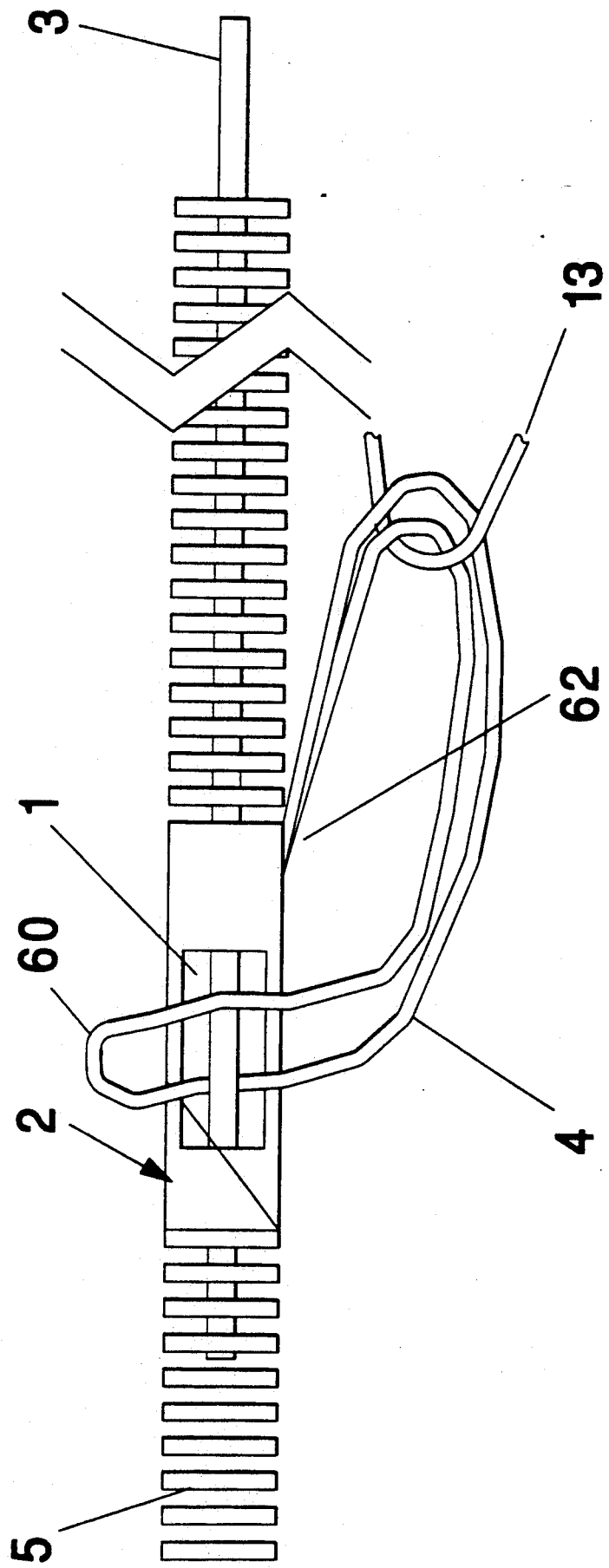
FIG. 34 is a perspective view of still another example of the above device.

FIG. 34 shows a second example of the device for introducing a medium, such as the artificial blood vessel 7, into a human body. The device includes a flexible metallic tube 2 having a front end. The flexible metallic tube 2 is formed with a side window 1 adjacent the front end. The device includes a wire 3 which is slidably inserted through the tube 2, and through the front end of the tube, so as to extend along the side window 1 of the tube 2. The tube 2 is intended to be inserted through the medium and into a human body. The device includes at least one string 4 having a first end fixed to the tube 2 adjacent the side window 1. The at least one string 4 is arranged so as to be passed through the medium and wound around the wire 3 where the wire 3 extends along the side window 1 of the tube 2. In this embodiment, the at least one string has a second end which is fixed to tube 2 adjacent the side window 1 so as to form a loop 60 through which the wire 3 is passed. The first end of the string and the second end of the string can be twisted together to form a single twisted terminal end 62. In this embodiment, the medium has a front opening provided with at least one loop 13 through which the string 4 is passed. In this embodiment, the tube 2 is provided at its front end with a short flexible guide tube 5 and at its rear end with a long flexible guide tube 6. The short and long guide tubes 5 and 6 can be a coil spring made of soft metal or synthetic resin such as polyethylene, or a tube made of soft synthetic resin or rubber. With the short and long flexible guide tubes 5 and 6 provided at the front and rear ends, respectively, of the tube 2, when the tube 2 is inserted into a meandrous blood vessel, the flexible front and rear guide tubes can move smoothly and easily along the meandrous blood vessel without danger of injuring the inner wall of the blood vessel 9.

FIG. 35 shows a third example of the device for introducing a medium, such as the artificial blood vessel 7, into a human body. The device includes a flexible metallic tube, having a front end, formed with a side window adjacent the front end. The device includes a wire 3 which is slidably inserted through the tube, and through the front end of the tube, so as to extend along the side window of the tube. The tube is intended to be inserted through the medium and into a human body. In this embodiment, the device includes two strings 4. Both of the strings 4 have a first end fixed to the tube adjacent the side window. The two strings 4 are arranged so as to be passed through the medium and wound around wire 3, where wire 3 extends along the side window of the tube. In this embodiment, each of the two strings 4 have a second end, each of which is twisted about their respective first ends to form two combined twisted terminal ends which are both fixed to the tube adjacent the side window so as to form a pair of loops 64 through which the wire 3 is passed. It is not necessary that the first end of the strings 4 and the second end of the strings 4 be twisted together to form a two twisted terminal ends in order to form the pair of loops 64. In this embodiment, the medium has a front opening provided with two loops 13 through which the strings 4 are passed. In this example, the tube is provided at the front end thereof with a soft, flexible guide tube 5. Flexible guide tube 5 can be a coil spring made of soft metal or synthetic resin such as polyethylene, or a tube made of soft synthetic resin or rubber. The soft, flexible tube 5 provided on the front end of the tube is intended to prevent the tube from injuring the inner wall of the blood vessel 9.

POSSIBLE APPLICATION IN INDUSTRY

As mentioned above, the appliance collapsible for insertion into human organs and capable of resilient restoration constructed in accordance with the invention is useful as an artificial blood vessel or in expanding constricted parts in human organs. The device of the invention is useful in collapsing the appliance, inserting the collapsed appliance into a catheter and releasing the appliance therefrom at a required position in the human body.

While there is shown and described herein certain specific structures embodying this invention for the purpose of clarity of understanding, the same is to be considered as illustrative in character, it being understood that only preferred embodiments have been shown and described. It will be manifest to those skilled in the art that certain changes, various modifications and rearrangements of the parts may be made without departing from the spirit and scope of the underlying inventive concept and that the same is not limited to the particular forms herein shown and described except insofar as indicated in the scope of the appended claims.

What is claimed is:

1. A device for introducing a medium into a human body comprising:
   a tube having a front end, wherein said tube is formed with a side window adjacent its front end, said tube to be inserted through said medium;
   a wire inserted through said tube and through said front end of said tube so as to extend along said side window of said tube; and
   at least one string, said at least one string having a first end, said first end of said string being fixed to said tube adjacent said side window, said string being arranged so as to be passed through said medium and wound around said wire where said wire extends along said side window of said tube.

2. A device for introducing a medium into a human body, as described in claim 1, further comprising a flexible guide tube connected to said front end of said tube.

3. A device for introducing a medium into a human body, as described in claim 2, wherein said flexible guide tube further comprises a coil spring.

4. A device for introducing a medium into a human body, as described in claim 1, further comprising a short flexible guide tube connected to said front end of said tube and a long flexible guide tube connected to a rear end of said tube.

5. A device for introducing a medium into a human body, as described in claim 4, wherein said short flexible guide tube further comprises a coil spring, and wherein said long flexible guide tube further comprises a coil spring.

6. A device for introducing a medium into a human body, as described in claim 1, wherein said medium has a front opening provided with at least one loop through which said string is passed.

7. A device for introducing a medium into a human body, as described in claim 1, wherein said at least one string is wound about said wire at said side window, and wherein said at least one string further comprises a second end, said second end being nipped between said tube and said wire so as to be held by said tube and said wire.

8. A device for introducing a medium into a human body, as described in claim 7, wherein said second end of said at least one string is formed into a knot.

9. A device for introducing a medium into a human body, as described in claim 1, wherein said at least one string further comprises a second end wherein said second end is fixed to said tube adjacent said side window so as to form a loop through which said wire is passed.

10. A device for introducing a medium into a human body, as described in claim 9, wherein said first end of said string and said second end of said string are twisted together.

* * * * *